(12) United States Patent
Yatabe et al.

(10) Patent No.: US 7,846,125 B2
(45) Date of Patent: Dec. 7, 2010

(54) SPRAYER

(75) Inventors: Teruyuki Yatabe, Ashigarakami-gun (JP); Koichi Hayakawa, Ashigarakami-gun (JP); Kenji Yokoyama, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 184 days.

(21) Appl. No.: 12/120,041

(22) Filed: May 13, 2008

(65) Prior Publication Data
US 2008/0294099 A1 Nov. 27, 2008

(30) Foreign Application Priority Data
May 23, 2007 (JP) .............................. 2007-137119

(51) Int. Cl.
*A61M 37/00* (2006.01)
(52) U.S. Cl. .......................... 604/24; 604/311; 604/246
(58) Field of Classification Search .................. 604/82, 604/246, 258, 24
See application file for complete search history.

(56) References Cited

U.S. PATENT DOCUMENTS

| 5,755,362 | A | 5/1998 | Rodriguez, Jr. et al. | |
|---|---|---|---|---|
| 6,464,663 | B1 | 10/2002 | Zinger | |
| 2006/0189944 | A1* | 8/2006 | Campbell et al. | 604/191 |

FOREIGN PATENT DOCUMENTS

| AU | 199646544 A | 9/1996 |
|---|---|---|
| AU | 199874271 A | 9/1998 |
| BR | 199808323 A | 5/2000 |
| CA | 2212734 A1 | 9/1996 |
| DE | 19709896 C1 | 12/1998 |
| DE | 69612483 D1 | 5/2001 |
| DE | 69612483 T2 | 3/2002 |
| EP | 812238 A1 | 12/1997 |
| EP | 966330 A1 | 12/1999 |
| EP | 812238 B1 | 4/2001 |

(Continued)

OTHER PUBLICATIONS

U.S. Appl. No. 12/068,533, filed Feb. 7, 2008 naming Kenji Yokoyama and Koichi Hayakama as inventors.

(Continued)

*Primary Examiner*—Nicholas D Lucchesi
*Assistant Examiner*—Leah Stohr
(74) *Attorney, Agent, or Firm*—Buchanan Ingersoll & Rooney PC

(57) ABSTRACT

A sprayer includes a nozzle through which gas is to be ejected with positiveness and uniformity. The sprayer is provided with a nozzle having inner tubes through the interior of which liquid is to pass and an outer tube receiving the inner tubes therein and allowing gas to pass through a space defined with the inserted inner tubes. The inner tubes have respective liquid orifices through which liquids are to be ejected. The outer tube is arranged therein with the liquid orifices and a gas orifice for ejecting gas. When the nozzle is viewed from front, the outer peripheries of the liquid orifices each assume a circular form while the inner peripheries of the gas orifices are differently shaped to provide plural point contact between the outer periphery of the liquid orifice and the inner periphery of the gas orifice.

12 Claims, 15 Drawing Sheets

FOREIGN PATENT DOCUMENTS

| | | |
|---|---|---|
| JP | 07-100209 A | 4/1995 |
| JP | 09-296039 A | 11/1997 |
| JP | 11-502464 A | 3/1999 |
| JP | 11502464 T | 3/1999 |
| JP | 2001-057979 (A) | 3/2001 |
| JP | 2001-515401 A | 9/2001 |
| JP | 2001515401 T | 9/2001 |
| JP | 2002-282368 A | 10/2002 |
| JP | 2005-152790 A | 6/2005 |
| JP | 3799414 B2 | 7/2006 |
| WO | WO 95/31138 A1 | 11/1995 |
| WO | WO 9626790 A1 | 9/1996 |
| WO | WO 9840167 A1 | 9/1998 |

OTHER PUBLICATIONS

U.S. Appl. No. 12/199,880, filed Aug. 28, 2008, Yokoyama.
U.S. Appl. No. 12/265,498, filed Nov. 5, 2008, Hayakawa.

\* cited by examiner

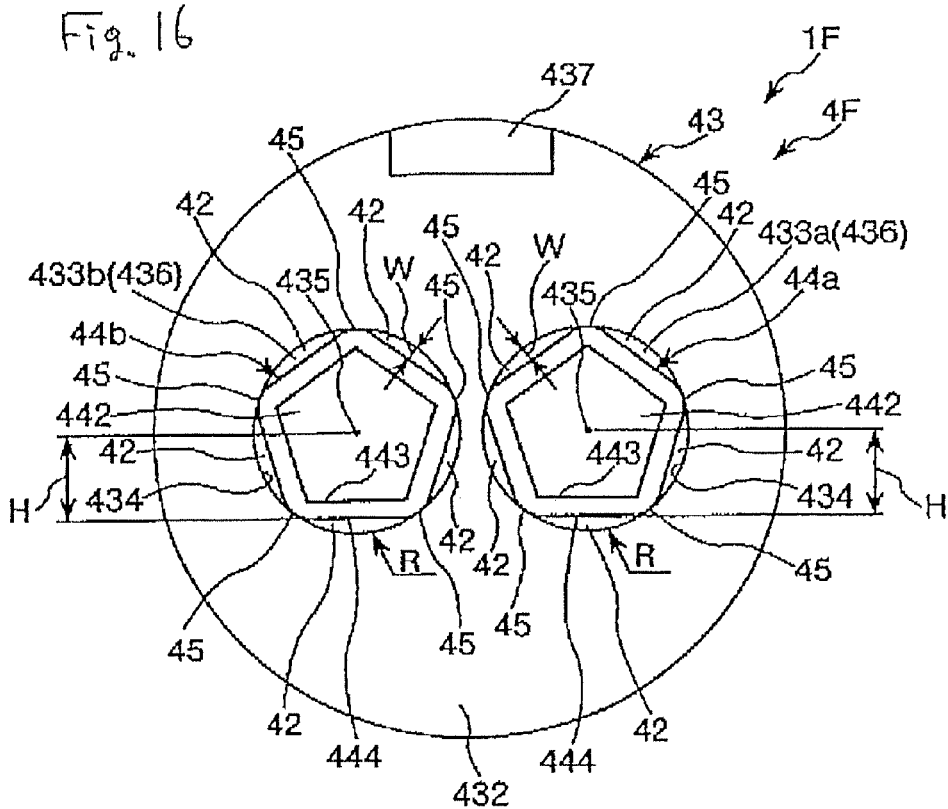
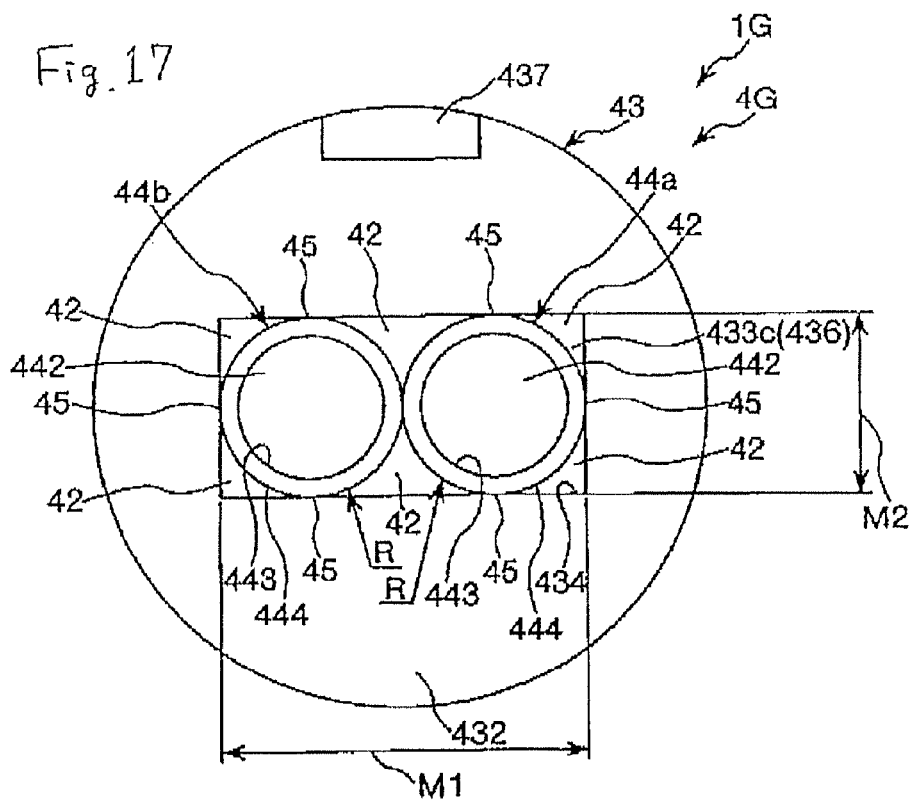

SPRAYER

TECHNOLOGICAL FIELD

The present invention generally relates to a device for delivering a liquid material. More specifically, the invention pertains to a sprayer having useful application in the medical field for spraying a liquid at a body region.

BACKGROUND DISCUSSION

Sprayers have been developed in the past for mixing two or more liquids to form an anti-adhesive material or a living tissue adhesive and ejecting the mixture to a diseased region of a body.

Known sprayers like this are structured to feed ingredients, solidifiable upon mixed, e.g. a solution containing thrombin and a solution containing fibrinogen, to a diseased region or nearby in a separated state and to apply those while being mixed at the diseased region.

Existing sprayers include a nozzle having inner tubes connected to the spouts of two syringes respectively containing different types of liquids, and an outer tube receiving the inner tubes and allowing sterilized gas to pass through a space with the inner tubes. An example of this sprayer is disclosed in JP-A-2001-57979. Sterilized gas is supplied from a bombe connected to the outer tube through a tube and filled with sterilized gas.

The inner tubes, in the nozzle of the sprayer described in JP-A-2001-57979, each have a liquid orifice opening at a tip through which liquid is to be ejected. The outer tube has two gas orifices opening at a tip for ejecting sterilized gas and arranged therein with the liquid orifices. In this manner, the nozzle of the sprayer described in JP-A-2001-57979 is of a double-tube structure in which the liquid orifices and the corresponding gas orifices are arranged concentrically. Clearances (gaps) are each formed between the liquid orifice and the corresponding gas orifice.

When liquids are ejected together with sterilized gas in the nozzle constructed as noted above, it is possible that the liquid orifices will become eccentric (i.e., will deflect) relative to the gas orifice under a certain condition of pressure and flow rate of sterilized gas and flow rate of each liquid, for example. In this state, the clearance is configured with greater and smaller portions, thus resulting in nonuniform ejection of sterilized gas, i.e., an uneven ejection of sterilized gas.

To prevent this eccentricity of the liquid orifice relative to the gas orifice so as to eject the sterilized gas with relative uniformity, one possibility to consider is to provide a plurality of ribs (convexes) in the inner peripheral surface of the gas orifice which abut against the outer peripheral surface of the liquid orifice and sustain the liquid orifice, with the ribs being arranged intermittently in the clearance.

However, there is a need to form a clearance microscopic in dimension (e.g. smaller than 150 μm) in order to enable relatively uniform ejection of sterilized gas. Thus, it is quite difficult, if not impossible, to provide ribs with accuracy in a manner not to obstruct the relatively uniform ejection of sterilized gas. For example, size variation might result in a plurality of ribs or clearance be filled up by ribs in the course of forming the ribs.

SUMMARY

According to one aspect, a sprayer having a front end comprises a sprayer body on which are mounted a first liquid-containing tube containing a first liquid and a second liquid-containing tube containing a second liquid whose composition differs from a composition of the first liquid, and a nozzle extending forwardly from the sprayer body. The nozzle comprises a first inner tube connected to the liquid-containing first tube and through which is to flow the first liquid, a second inner tube connected to the liquid-containing second tube and through which is to flow the second liquid, and an outer tube having an interior in which is positioned the first and second tubes, wherein the outer tube being adapted to be connected to a gas source to supply gas to the interior of the outer tube. The outer tube comprises a front wall positioned at a front tip of the outer tube, the front wall is provided with a through opening forming a gas orifice through which the gas supplied to the interior of the outer tube is to be ejected, and the first inner tube has a tip end positioned in the gas orifice. The inner periphery of the gas orifice and the outer periphery of the tip end of the first inner tube are differently configured relative to one another such that the outer periphery of the tip end of the first inner tube and the inner periphery of the gas orifice contact one another at a plurality of circumferentially spaced apart contact points separated from one another by spaces between the outer periphery of the first inner tube and the inner periphery of the gas orifice.

In accordance with another aspect, a sprayer having a front end from which a composition is sprayed comprises inner tubes through which is adapted to pass liquid to form the composition, and an outer tube having an interior in which is positioned at least a first one of the inner tubes and through which gas is adapted to flow. The first inner tube possesses a liquid orifice opening at the tip end of the first inner tube from which the liquid is adapted to be ejected. The outer tube possesses a gas orifice opening at the tip end of the outer tube from which the gas is adapted to be ejected. The liquid orifice, viewed from the front end of the sprayer, possesses an outer periphery that is circular in shape, and the gas orifice, viewed from the front end of the sprayer, possesses an inner periphery that is polygonal in shape, including polygonal in shape with rounded corners. The outer periphery of the liquid orifice and the inner periphery of the gas orifice are in point contact with each other at a plurality of spaced apart contact points so that the liquid orifice is fixed in position relative to the gas orifice, with a space between the outer periphery of the liquid orifice and the inner periphery of the gas orifice at regions between circumferentially adjacent contact points.

In accordance with a still further aspect, a sprayer having a front end from which a composition is sprayed comprises inner tubes through which is adapted to pass liquid to form the composition, and an outer tube having an interior in which is positioned at least a first one of the inner tubes and through which gas is adapted to flow. The first inner tube possesses a liquid orifice opening at a tip end of the first inner tube from which the liquid is adapted to be ejected, and the outer tube possesses a gas orifice opening at the tip end of the outer tube from which the gas is adapted to be ejected. The liquid orifice, viewed from the front end of the sprayer, possesses an outer periphery that is polygonal in shape, including polygonal in shape with rounded corners, and the gas orifice, viewed from the front end of the sprayer, possesses an inner periphery that is circular in shape. The outer periphery of the liquid orifice and the inner periphery of the gas orifice are in point contact with each other at a plurality of circumferentially spaced apart contact points so that the liquid orifice is fixed in position relative to the gas orifice, with a space between the outer periphery of the liquid orifice and the inner periphery of the gas orifice at regions between circumferentially adjacent contact points.

With the sprayer disclosed here, point contact is provided at a plurality of points between the inner periphery of the gas orifice and the outer periphery of the liquid orifice. This helps positively restrict the liquid orifice from deflecting radially thereof, for example, under the pressure of gas when liquid is ejected together with gas through the nozzle, i.e. the liquid orifice is positively fixed relatively to the gas orifice. This can help maintain a constant size of gaps between the inner periphery of the gas orifice and the outer periphery of the liquid orifice, thereby positively uniformly ejecting gas through the gaps. Also, by receiving the inner tubes in the outer tube and further fitting the gas orifice of the outer tube and the liquid orifices of the inner tubes together, a nozzle can be relatively easily manufactured with point contact being provided at a plurality of points between the inner periphery of the gas orifice and the outer peripheries of the liquid orifices.

BRIEF DESCRIPTION OF THE DRAWING FIGURES

FIG. 16 is a front view of a nozzle of a sprayer according to a seventh embodiment.

FIG. 17 is a front view of a nozzle of a sprayer according to an eighth embodiment.

DETAILED DESCRIPTION

Figure 7:
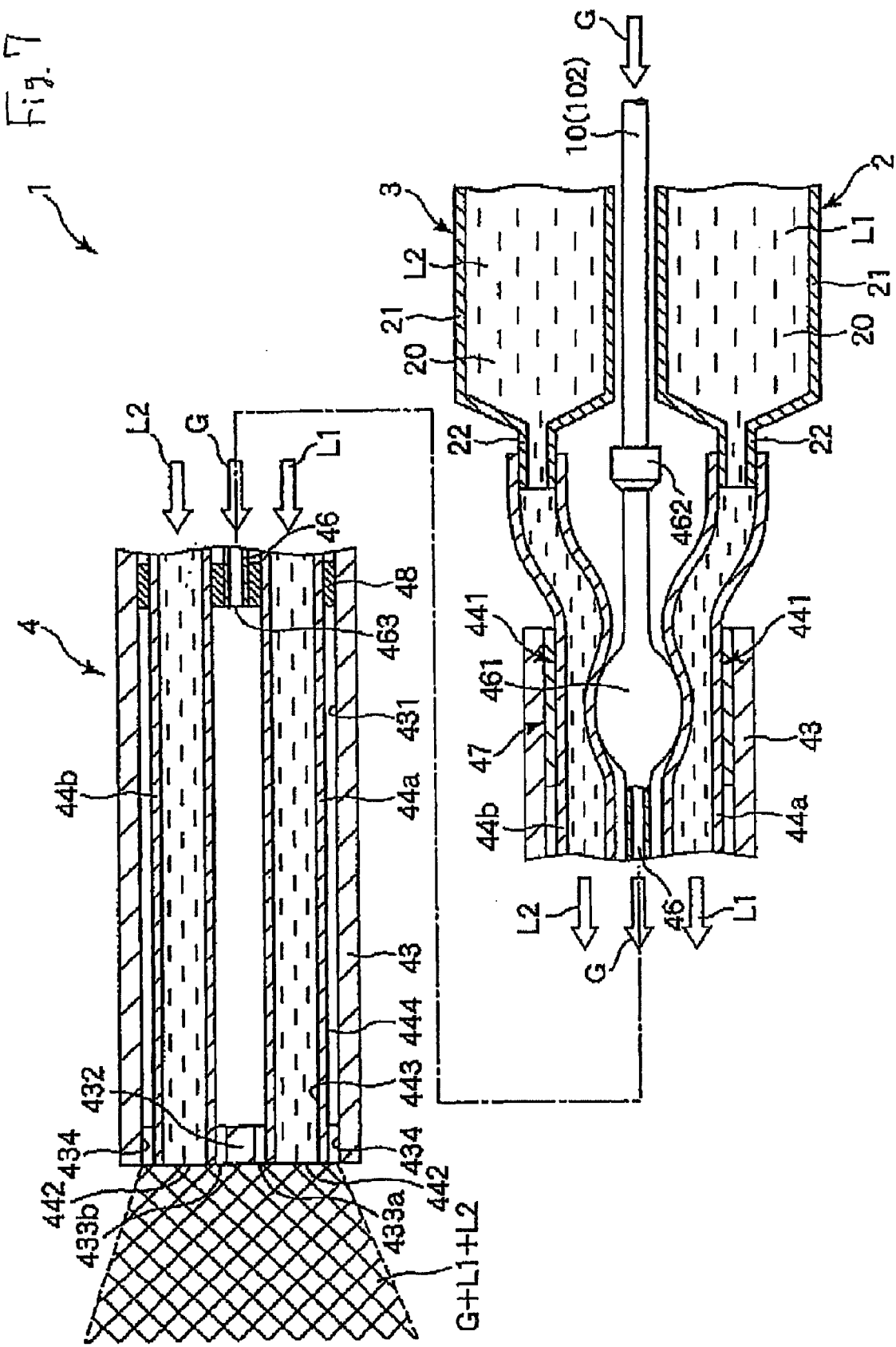
FIG. 7 is a fragmentary longitudinal cross-sectional view of the nozzle and syringe of the sprayer shown in FIG. 1, illustrating parts of the sprayer in another operational state.
Figure 8:
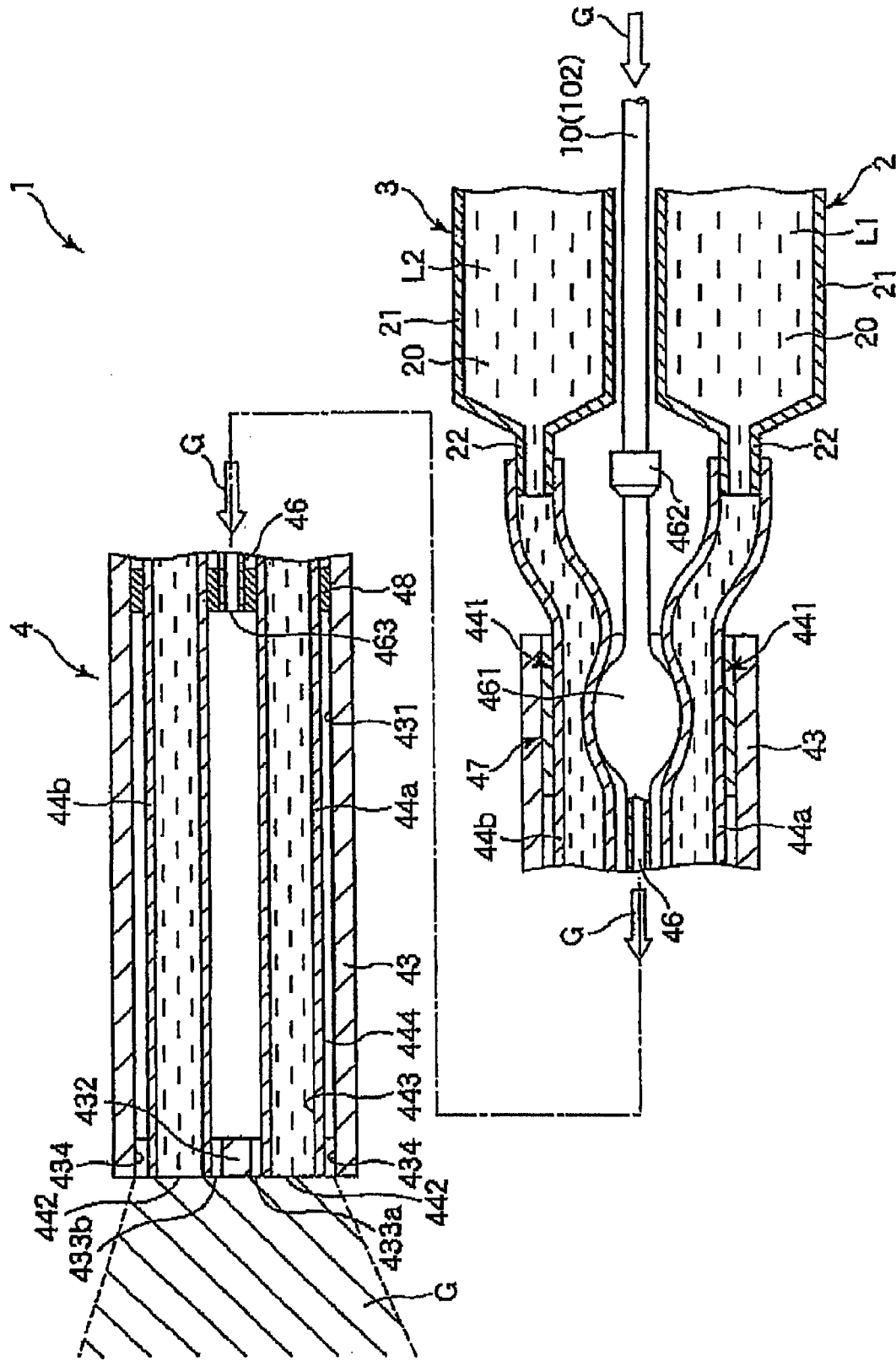
FIG. 8 is a fragmentary longitudinal cross-sectional view of the nozzle and syringe of the sprayer shown in FIG. 1, illustrating parts of the sprayer in another operational state.
Figure 9:
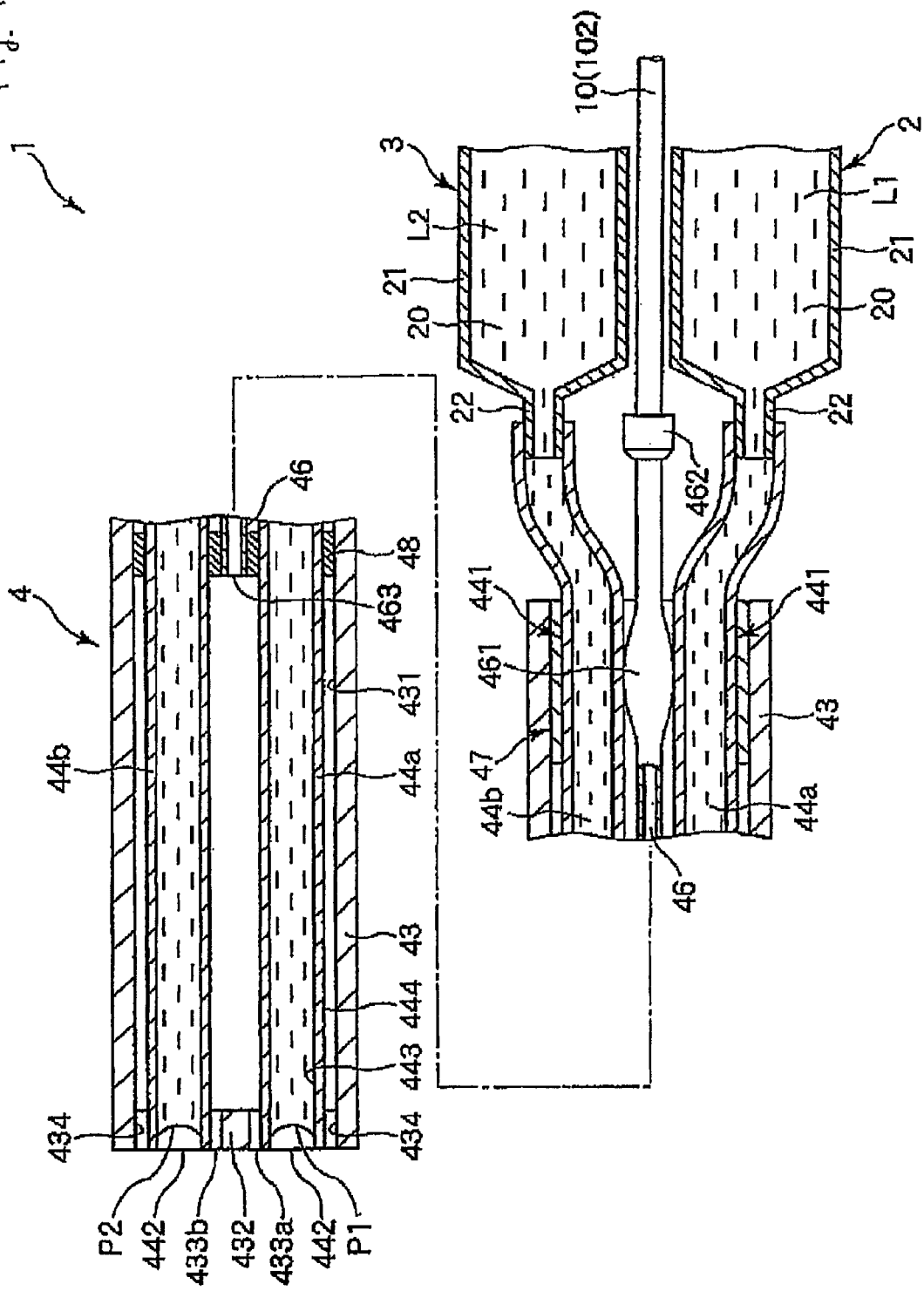
FIG. 9 is a fragmentary longitudinal cross-sectional view of the nozzle and syringe of the sprayer shown in FIG. 1, illustrating parts of the sprayer in another operational state.
Figure 19:
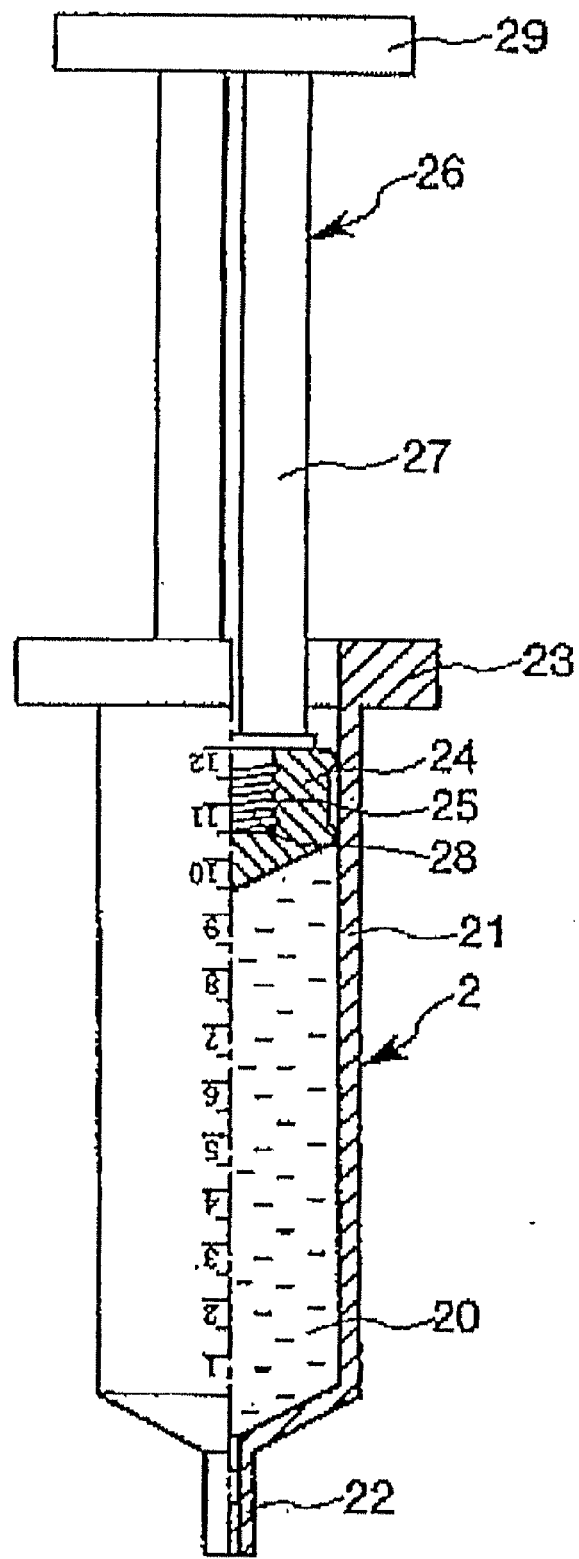
FIG. 19 is a longitudinal cross-sectional view of a first syringe (the same as a second syringe) to be mounted on the sprayer shown in FIG. 1.

FIGS. 1-10 illustrate one embodiment of the sprayer disclosed here, and FIG. 19 illustrates one of the two syringes to be mounted on the sprayer, it being understood that the other syringe is configured in the same way as that illustrated in FIG. 9. For the sake of explanatory convenience, the left and right sides are respectively referred to as the "front" and "rear (base)" in FIGS. 1, 2 and 5-9, while the lower and upper sides are respectively referred to as the "front" and "rear (base)" in FIG. 19. Also, the upper and lower sides are respectively referred to as "upper" or "forward upper" and "lower" or "forward lower" in FIGS. 1-4.

Figure 1:
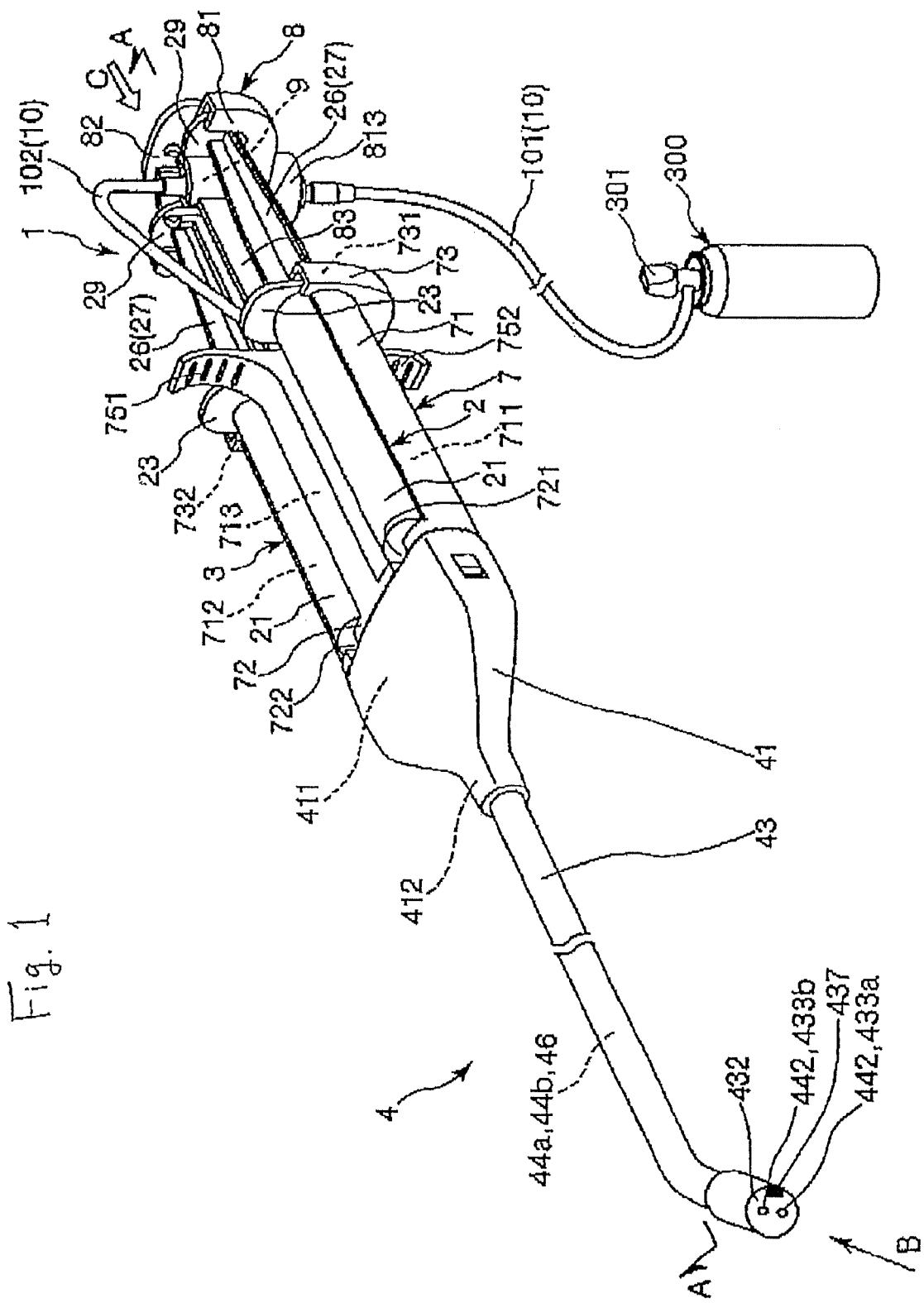
FIG. 1 is a perspective view of a sprayer according to a first embodiment disclosed herein.
Figure 2:
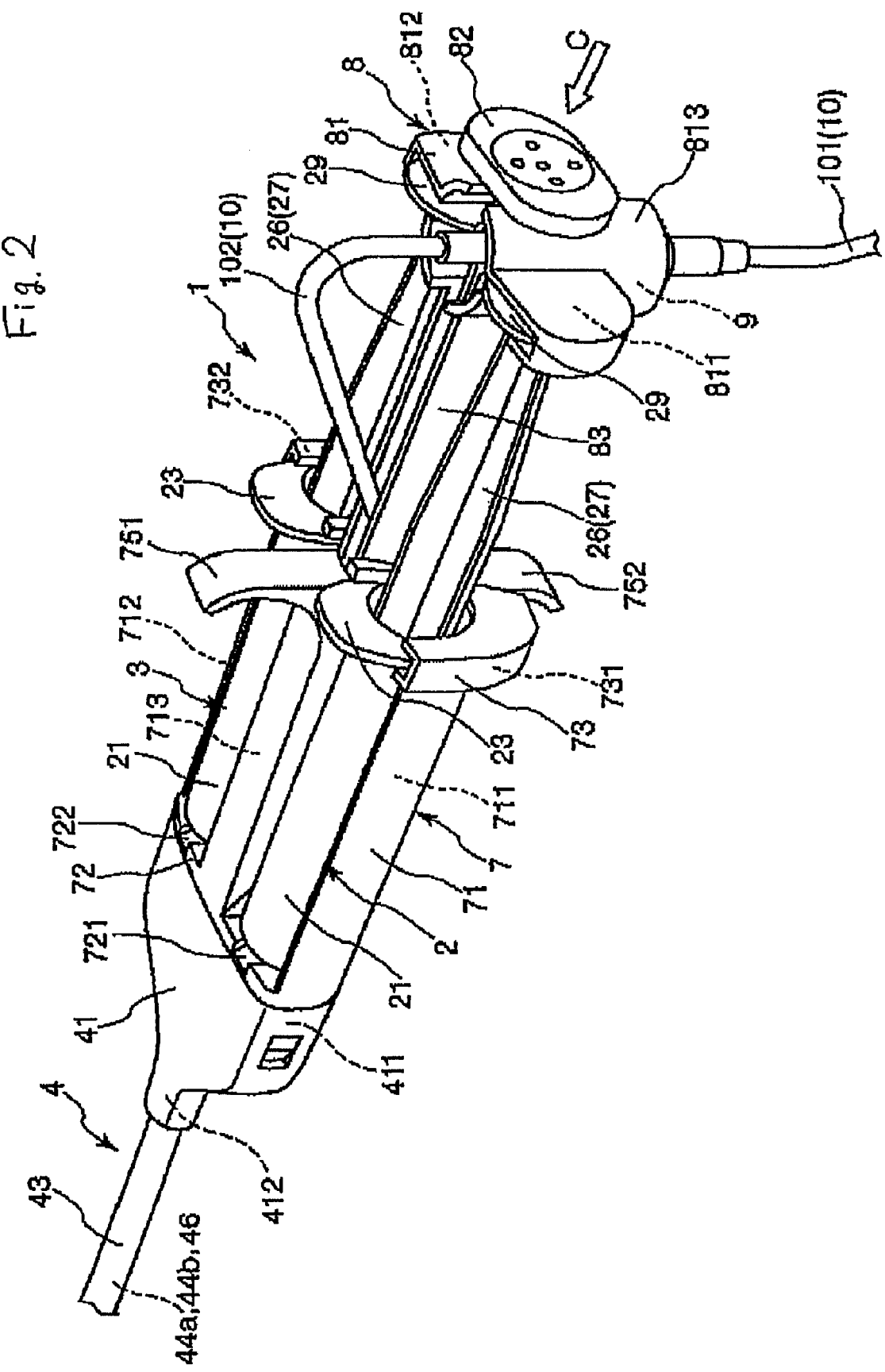
FIG. 2 is a perspective view of the sprayer shown in FIG. 1.

The sprayer 1 disclosed here is used to mix together two liquids (first liquid L1 and second liquid L2), different in composition from one another, and apply the resulting mixed liquid or composition. As shown in FIGS. 1 and 2, the sprayer 1 is used with a first liquid-containing tube 2 (first syringe), forming a liquid supply means, and a second liquid-containing tube 3 (second syringe) forming a liquid supply means. The first syringe 2 and the second syringe 3 are mounted and contain the first liquid L1 and the second liquid L2, respectively.

Referring to FIG. 19 which illustrates the first syringe 2, whose construction is the same as the second syringe 3, a liquid (first liquid) L1 is filled in a space (reservoir space) 20 enclosed by an outer shell 21 and a gasket 24 prior to being mounted on the sprayer 1. The second liquid L2 is filled in the corresponding space 20 of the second syringe 3.

The first liquid L1 to be filled in the first syringe 2 and the second liquid L2 to be filled in the second syringe 3 are different in their compositions (ingredients) from one another. The first and second liquids L1, L2 are suitably selected in accordance with the application and use or purpose of the sprayer 1, the condition being treated, etc.

For example, where used to administer an anti-adhesion material, one of the first and second liquids L1, L2 may contain carboxymethy dextrin modified with succinimidyl while the other may contain disodium hydrogenphosphate. First and second liquids L1, L2, in such a combination, change in quality, or gelatinize, if mixed together. Of course, it is to be understood that the types and combinations of first and second liquids L1, L2 are not limited to those just mentioned or otherwise described.

By pushing the respective plungers 26 of the first and second syringes 2, 3, the first and second liquids L1, L2 are supplied respectively to first and second inner tubes 44a, 44b of a nozzle 4, discussed in more detail below, with relative easiness and positiveness. The respective plungers 26 are pushed manually by the operator of the sprayer 1. Consequently, the operator is allowed to apply a liquid mixture in his/her desirable timing.

The sprayer 1, mounted with the first and second syringes 2, 3 respectively filled with the first and second liquids L1, L2, includes a sprayer body 7, the nozzle 4, a manipulator 8, a valve mechanism 9 serving as an opening/closing means, and a gas tube (gas passage) 10 connected to a gas-containing canister or container 300 serving as a gas supply means for supplying gas.

The gas-containing canister 300 is first explained prior to describing various parts constituting the sprayer 1. The gas-containing canister 300 contains or is filled with sterile gas G (hereinafter referred to as "gas G") under pressure (compressed) within the interior space thereof so that gas G can be supplied to the sprayer 1, more specifically the nozzle 4 of the sprayer 1. The gas-containing canister 300 is arranged with an opening-and-closing valve (cock) 301 that opens and closes to control the supply/non-supply of gas G to sprayer 1. When using the sprayer 1, the valve 301 is opened. The type of gas G in the gas-containing canister 300 is not especially limited, but may be carbon dioxide, for example.

As shown in FIGS. 1 and 2, the sprayer body 7 is configured to receive the syringes 2, 3 and position them in side-by-side relation (in parallel) to one another. The sprayer body 7 includes a base 71, a front plate (first engager) 72 provided in the front of the base 71, a rear plate (second engager) 73 provided in the rear of the base 71, and two handles 751, 752 provided in the vicinity of the rear plate 73 of the base 71.

The base 71 is provided with receiving areas that are configured to receive the syringes. In this disclosed embodiment, the receiving areas are in the form of recesses or concave regions 711, 712 that are semicircular in cross-section and arranged side-by-side in the upper portion of the base. The first syringe 2 (i.e., the outer shell 21 of the first syringe 2) is received in the recess 711 while the second syringe 3 (i.e., the outer shell 21 of the second syringe 3) is received in the recess 712.

As mentioned above, the front plate 72 is provided at the front of the base 71. The front plate 72 includes grooves 721, 722 in positions respectively corresponding to the recesses 711, 712. Each of the first and second syringes 2, 3 possesses a diameter-reduced portion 22 at its forward end. To mount the first and second syringes 2, 3 in the sprayer, the diameter-reduced portion 22 of the first syringe 2 is received in the groove 721, while the diameter-reduced portion 22 of the second syringe 3 is received in the groove 722.

A rear plate 73 is provided at the rear of the base 71. The rear plate 73 is formed with recesses 731, 732 at positions respectively corresponding to the recesses 711, 712 of the base 71. To mount the first and second syringes 2, 3, the flange 23 (base) of the first syringe 2 engages or is inserted into the recess 731 while the flange 23 (base) of the second syringe 3 engages or is received in the recess 732.

The first and second syringes 2, 3 are positively fixed side by side in the sprayer body 7 by engaging the diameter-reduced portions 22 with the front plate 72 and by engaging the flanges 23 with the rear plate 73.

The two handles 751, 752 are provided in the vicinity of the rear plate of the base 71. The handles 751, 752 are configured in a manner allowing the operator to put his/her fingers thereon during use of the sprayer 1. One of the handles 751 is constructed as an upwardly protruding or extending plate piece, while the other handle 752 is constructed as a downwardly extending or protruding plate piece. The front surface of each handle 751, 752 which faces to the front is arcuate in shaped, possessing a curved convex form.

Various parts constituting the sprayer body 7 may be formed integrally or may be constructed separately one from another. Also, the material of which the sprayer body 7 is formed is not particularly limited. Examples of suitable materials include a metallic material, e.g. aluminum or stainless steel, or plastic. The metallic and plastic materials can be used individually or in combination.

A manipulator 8 is arranged in the rear of the sprayer body 7 and is movable in the longitudinal direction relative to the sprayer body 7. The manipulator 8 is a part that pushes the plungers 26, 26 of the first and second syringes 2, 3 in the forward direction toward the front (i.e., in the direction of the arrow C in FIGS. 1, 2 and 4). The manipulator 8 includes a coupler 81 that couples together the flanges 29 of the plungers 26 of the first and second syringes 2, 3, a presser 82 located rearwardly of the coupler 81, and a rail 83 extending from the coupler 81 toward the front.

The coupler 81 is provided with recesses 811, 812 which both open upwardly. The recess 811 is in a form corresponding to the flange 29 of the plunger 26 of the first syringe 2 so that such flange 29 can be engaged therewith as shown in FIG. 2. Meanwhile, the other recess 812 is in a form corresponding to the flange 29 of the plunger 26 of the second syringe 3 so that the flange 29 of the plunger 26 of the second syringe 3 can be engaged therewith as seen in FIG. 2.

By virtue of the coupler 81, positive coupling and fixing exists between the flanges 29 of the plungers 26 of the first and second syringes 2, 3. The plungers 26 can thus be moved together integrally at one time in the direction indicated by the arrow C.

The coupler 81 is provided with a cylindrical portion 813 forming a cylinder located between the one recess 811 and the other recess 812. The cylindrical portion 813 is positioned such that the axis of the cylindrical portion 813 is vertically oriented or is parallel with the vertical direction as shown in FIGS. 1 and 2. The cylindrical portion 813 receives the valve means 9.

The elongate rail 83 extends from the outer periphery of the cylindrical portion 813 of the coupler 81 in the forward direction (i.e., towards the front). The rail 83 is provided in the base 71 of the sprayer body 7 and is inserted or positioned in the guide 713 formed in an elongate form. By pushing the manipulator 8 in the direction of the arrow C, the rail 83 is guided along the guide 713. This allows for a relatively smooth pushing operation.

A plate-like pusher 82 is provided at the rear of the cylindrical portion 813 of the coupler 81. The plate-like pusher 82 is adapted to move lengthwise of the sprayer body 7.

The pusher 82 is a part pressed by the operator during use of the sprayer 1, i.e. upon applying a mixed liquid to a treatment region, diseased region, etc. When using the sprayer 1, the user's index finger is put on the handle 751, the middle finger is placed on the handle 752 and the thumb is put on the pusher 82. This makes it possible to positively grip the sprayer 1 in a relatively stable manner. At the same time, the manipulator 8 (pusher 82) can be operated with smoothness and positiveness, thus improving the operability of the sprayer 1.

The pusher 82 is coupled to a second connecting portion 92 of the valve means 9, discussed in more detail below. The material forming the manipulator 8 is not limited to a particular material. Examples include materials such as those listed in the explanation of materials which can be employed in the application body 7.

As mentioned before, the valve means 9 is provided in cylindrical portion 813 of manipulator 8. The valve means 9 operates to open and close the gas G flow from the gas-containing canister 300 to the nozzle 4. Through the valve means 9, the first tube 101 and the second tube 102 are shut off as seen in FIG. 3 and communicated together as seen in FIG. 4 by the operation of the valve means 9.

Figure 3:
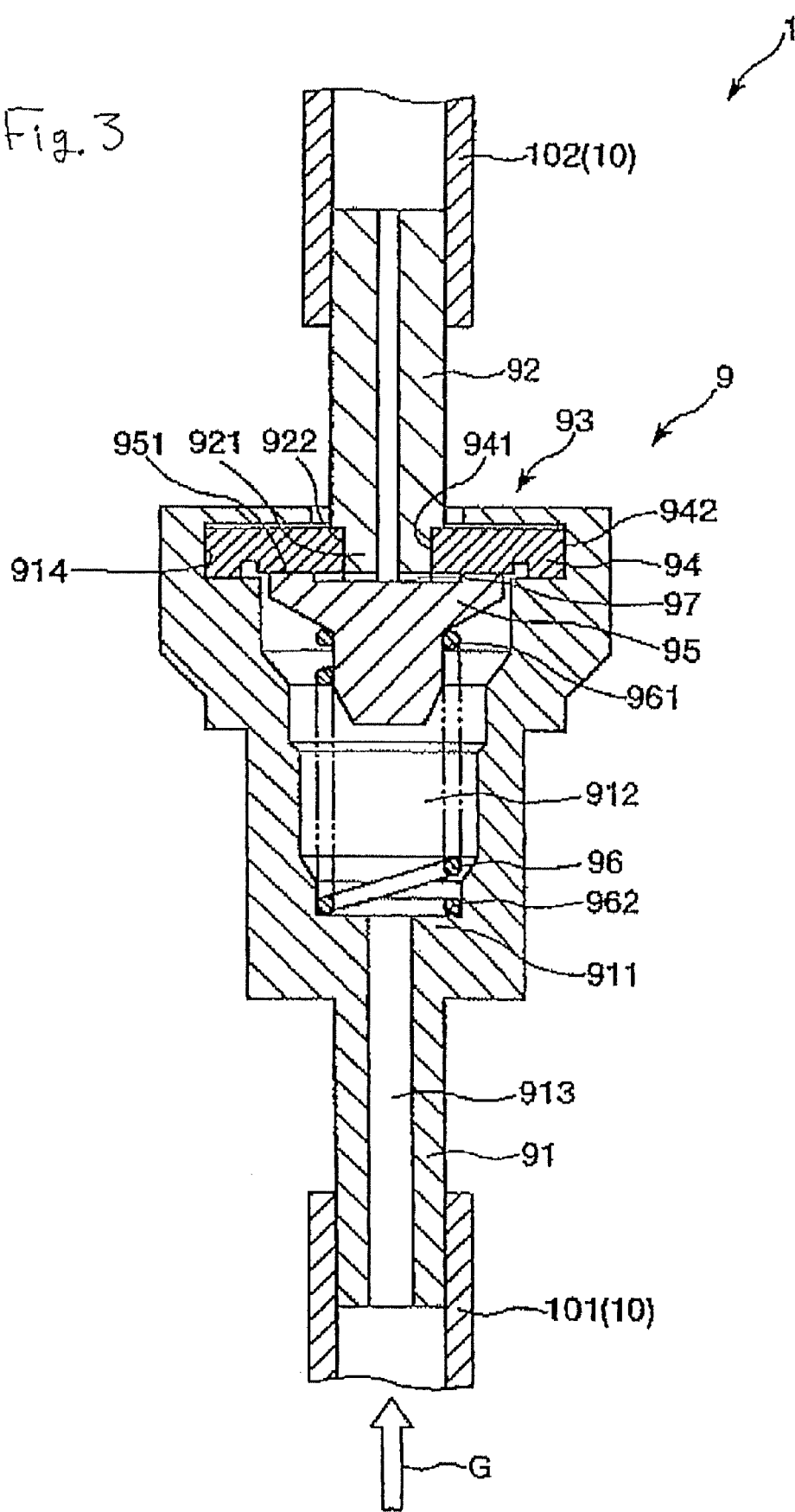
FIG. 3 is a cross-sectional view of the sprayer taken along the section line A-A in FIG. 1 illustrating the opening/closing means of the sprayer (in the closed state of the gas passage).
Figure 4:
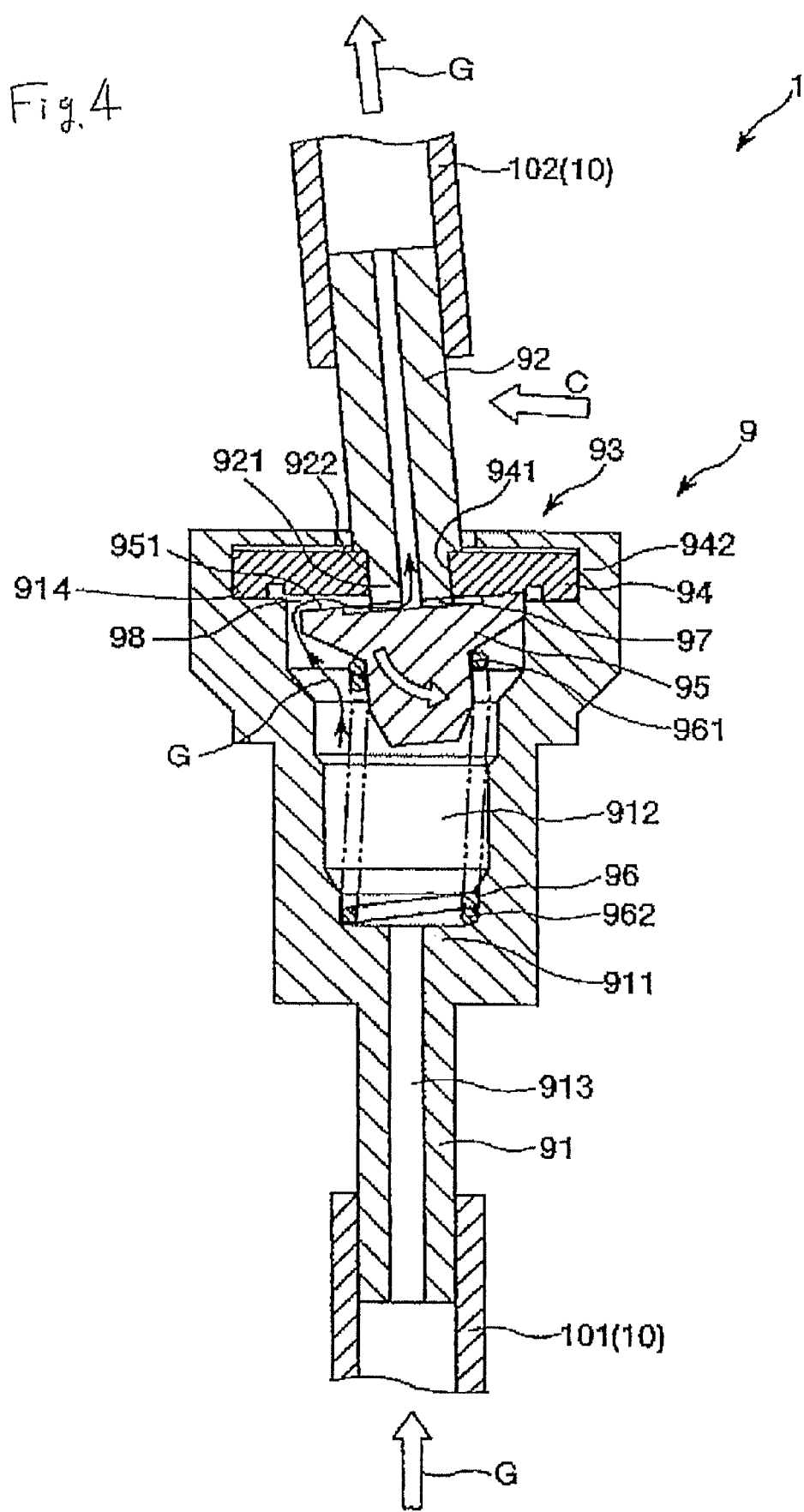
FIG. 4 is a cross-sectional view of the sprayer taken along the section line A-A in FIG. 1 illustrating the opening/closing means of the sprayer (in the opened state of the gas passage).

As shown in FIGS. 3 and 4, the valve means 9 has a first connecting portion 91 connected to the first tube 101, a second connecting portion 92 connected to the second tube 102, and an openable and closable valve 93 received in the first connecting portion 91.

The first connecting portion 91 is tubular in form and includes a lumen. The lumen of the first connecting portion 91 includes a container portion 912 (larger-diameter portion), located on the downstream side, and the valve 93. The lumen of the first connecting portion 91 also includes a diameter-reduced portion 913 having a diameter smaller than the inner diameter of the container portion 912 on the upstream side. A step 911, whose inner diameter sharply changes, is formed at the boundary between the diameter-reduced portion 913 and the container portion 912.

The second connecting portion 92 is tubular in form. As mentioned before, the second connecting portion 92 is coupled to the pusher 82 of the manipulator 8. The second connecting portion 92, whose lower end 921 is supported by the seal member 94 of the valve 93 (i.e., the lower end of the second connecting portion is received in a hole in the seal member 94), is arranged downstream of the first connecting portion 91 through the seal member 94. The second connecting portion 92 is arranged to be displaced between a first position (i.e., the state shown in FIG. 3) in which the axis of the second connecting portion 92 is in alignment relative to the axis of the first connecting portion 91 (i.e., the first and second connecting portions are coaxial) and a second position (i.e., the state shown in FIG. 4) in which the axis of the second connecting portion 92 is inclined in the direction of the arrow C (the operating direction) of the pusher 82 (manipulator 8) about the lower end 921. In this second position of the second connecting portion 92, the axis of the second connecting portion 92 is not in alignment relative to the axis of the first connecting portion 91 (i.e., the first and second connecting portions are not coaxial).

The seal member 94 of the valve 93 is constructed as an elastic material. The valve 93 includes the seal member 94, a flange 95 positioned upstream of the seal member 94, and a bias member 96 that biases the flange 95 toward the seal member 94.

The seal member 94 is in a link form, and has an inner periphery 941 in close contact with the outer periphery 922 of the lower end 921 of the second connecting portion 92. The seal member 94 has an outer periphery 942 in close contact with the inner periphery 914 of the container 912 of the first connecting portion 91. With the seal member 94 constructed in this way, the first connecting portion 91 and the second connecting portion 92 are hermetically coupled together through the seal member 94.

The flange 95 has an outer diameter greater than the outer diameter of the second connecting portion 92. The flange 95 is arranged oppositely to (in facing relation to) a lower end surface of the second connecting portion 92 through gap 97.

In this illustrated embodiment, the bias member 96 is a compression coiled spring. In the compressed state, its upper end 961 is in abutment against the flange 95 while the lower end 962 is in abutment against the step 911. This can positively bias the flange 95 toward the seal member 94.

With this illustrated and described embodiment of the valve 93, the flange 95 is biased by the bias member 96 and placed in hermetic contact with the seal member 94 as shown in FIG. 3 when the second connecting portion 92 is in a first position, i.e. when no external force is applied to the second connecting portion 92. This places the valve 93 in the closed state.

When a press force is applied in the direction of the arrow C to the second connecting portion 92 by the presser 82 of the manipulator 8, the second connecting portion 92 is displaced or moved from the first position to the second position. At this time, the flange 95 is displaced against the bias force of the bias member 96. As a result of this, at least a part of the periphery 951 of the flange 95 moves away from the seal member 94 to create a gap 98 with the seal member as seen in FIG. 4. Consequently, gas G flows from the first connecting portion 91 to the second connecting portion 92 through the gap 98. In other words, the valve 93 is positioned in the open state.

With the valve means 9 constructed in the manner described above by way of example, the valve 93 is allowed to positively open and close interactively with the pressing of the manipulator 8. By virtue of this, when the valve 93 is in the closed state, the gas G is positively shut off from flowing from the gas-containing canister 300 to the nozzle 4. When the valve 93 is in the open state, the gas G can be positively released to flow.

The material forming the first connecting portion 91, the second connecting portion 92, the flange 95 and the bias member 96 is not limited, but can include, for example, metal material or plastic, either individually or in combination.

The material forming the seal member 94 is also not limited to a specific material. Examples of suitable materials include rubber material of various types, e.g. natural or butyl rubber.

The nozzle 4 is arranged on the front plate 72 of the sprayer body 72. The nozzle 4 ejects or sprays the gas G passing through the tube 10, the first liquid L1 passing through the diameter-reduced portion 22 of the first syringe 2, and the second liquid L2 passing through the diameter-reduced portion 22 of the second syringe 3.

Referring to FIGS. 5-9, the nozzle 4 includes a first inner tube 44a connected to the diameter-reduced portion 22 of the first syringe 2 and through which the first liquid L1 is allowed to pass, a second inner tube 44b connected to the diameter-reduced portion 22 of the second syringe 3 and through which the second liquid L2 is allowed to pass, an outer tube 43 in which the first and second inner tubes 44a, 44b are received or positioned, a supply tube 46 connected to the second tube 102 and adapted to supply gas G to the interior of the outer tube 43, and a fixing member 41 (shown in FIG. 1) that fixes the nozzle 4 to the front plate 72 of the sprayer body 7.

The first tube 44a, the second tube 44b, the outer tube 43 and the supply tube 46 may be each structured of a rigid material, a non-rigid material, a resilient material or the like, having flexibility. In this embodiment, the material forming the second tube 44b, the outer tube 43 and the supply tube 46 is a flexible material. The material of first inner tube 44a is, for example, a non-rigid or rigid resin of various types, e.g. polyvinyl chloride, polyethylene or polypropylene, a rubber material in various types, e.g. natural rubber, butyl rubber or silicone rubber, or stainless steel or aluminum.

The first inner tube 44a and the second inner tube 44b are similar in structure and so the following explanation pertaining to the first inner tube 44a applies equally to the second inner tube 44b.

The first inner tube 44a is constructed as an elongate tubular member, whose base is connected to the diameter-reduced portion 22 of first syringe 2. The first inner tube 44a has a liquid orifice 442 that opens at the tip of the tube 44a. The liquid orifice 442 is a part through which the first liquid L1 is ejected (sprayed) that is issued out of the diameter-reduced portion 22 of the first syringe 2 when the plunger 26 of the first syringe 2 is pushed.

The first inner tube 44a is circular in cross-section at its inner periphery (inner peripheral surface) 443 and its outer periphery (outer peripheral surface) 444. Accordingly, the liquid orifice 442 is also circular in form at its inner periphery 443 and outer periphery 444 as shown in FIG. 10.

Figure 10:
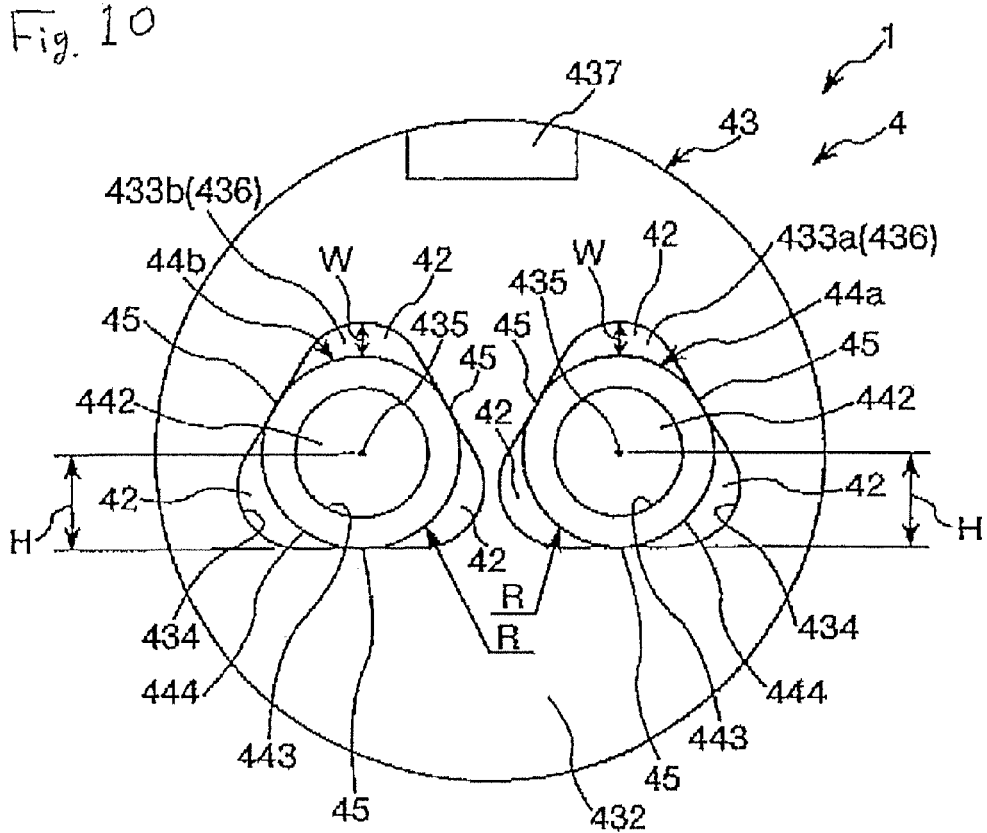
FIG. 10 is a front view of the nozzle of the sprayer shown in FIG. 1 as viewed from the direction of the arrow B in FIG. 1.

As shown in FIG. 10, the liquid orifice 442 possesses a tube wall thickness that is circumferentially constant. As a result, the liquid orifice 442 is positioned concentric relative to the inner periphery 443 and outer periphery 444 of the tube 44a.

As mentioned the second inner tube 44*b* is the same in structure to the first inner tube 44*a*.

Together with the first and second inner tubes 44*a*, 44*b* thus structured, the supply tube 46 is also received or positioned in the outer tube 43 as shown in FIGS. 5-9). The supply tube 46 is an elongate tubular member having a base 462 connected to the second tube 102. The base 462 is located between the respective bases of the first and second inner tubes 44*a*, 44*b* arranged side-by-side.

The supply tube 46 has a tip 463 positioned at an intermediate point of the outer tube 43. Gas G is ejected at the tip 463, thereby supplying gas G to the interior of the outer tube 43.

The tip 463 of the supply tube 46 is fixed in a liquid-tight manner with the outer peripheries of the first and second tubes 44*a*, 44*b* at a fixed portion, and the inner peripheral surface 431 of the outer tube 43 is fixed in a liquid-tight manner through a fixed portion 48 to the outer peripheries of the first and second tubes 44*a*, 44*b*.

This construction can help prevent troubles such as the first inner tube 44*a*, second inner tube 44*b* and supply tube 46 being twisted or kinked together when the sprayer 1 is being used. Accordingly, the tubes can be inhibited or prevented from being blocked due to such a trouble. Incidentally, the material forming the fixed portion 48 is not especially limited. Examples of suitable materials are those materials mentioned above in connection with the seal member 94.

The first inner tube 44*a*, the second inner tube 44*b* and the supply tube 46 are collectively received in the outer tube 43. The outer tube 43 is an elongate tubular member having a base connected to the front opening 412 of fixed member 41.

As mentioned before, the tip 463 of the supply tube 46 is positioned at an intermediate point of the outer tube 43 (i.e., an intermediate point considered with reference to the longitudinal extent of the outer tube 43) so that the gas G can be supplied to the interior of the outer tube 43 through the tip 463. The supplied gas G is able to pass or flow through the gaps between the outer tube 43, the first inner tube 44*a* and the second inner tube 44*b*.

As shown in FIGS. 5-9, the tip of the outer tube 43 includes a front wall 432. A gas orifice 436 (better shown in FIG. 10) constructed as two lumens 433*a*, 433*b* opens in the front wall 432. The two lumens 433*a*, 433*b* (gas orifice 436) are parts through which the gas G supplied from the supply pipe 46 is ejected (sprayed). As shown in FIG. 10, the lumens 433*a*, 433*b* each possess a (regular) triangular shape (cross-sectional shape) so that the inner periphery of the lumens 433*a*, 433*b* possesses a triangular shape (regular triangular shape) with rounded corners. The lumen 433*a* possessing this shape has a distance (length) H, between the center 435 of the lumen and the side (preferably the midpoint of the side), that is equal to or somewhat smaller than the radius R of the outer periphery 444 of the liquid orifice 442 of the first inner tube 44*a*.

The liquid orifice 442 of the first inner tube 44*a* is arranged in the interior of and concentrically to the lumen 433*a*, while the liquid orifice 442 of the second inner tube 44*b* is arranged in the interior of and concentrically to the lumen 433*b*. Because the positional relationship between the lumen 433*a* and the liquid orifice 442 of the first inner tube 44*a* is the same as the positional relationship between the lumen 433*b* and the liquid orifice 442 of the second inner tube 44*b*, the explanation of the positional relationship between the lumen 433*a* and the liquid orifice 442 of the first inner tube 44*a* applies equally to the positional relationship between the lumen 433*b* and the liquid orifice 442 of the second inner tube 44*b*.

As shown in FIG. 10, contact is provided at multiple points 45 (three points in this illustrated embodiment) between the inner periphery 434 of the lumen 433*a* and the outer periphery 444 of the liquid orifice 442 of the first inner tube 44*a*. When the first liquid L1 is ejected (sprayed) together with the gas G through the nozzle 4, the liquid orifice 442 is positively restricted from deviating radially (i.e., radially shifting), for example under the pressure of the gas G. The liquid orifice 442 is positively fixed relative to the lumen 433*a* (gas orifice 436). This maintains the gaps (clearances) between the inner periphery 434 of the lumen 433*a* (gas orifice) and the outer periphery 444 of the liquid orifice 442. The gaps or clearances are thus maintained constant. Accordingly, the gas G can be positively ejected in a uniform manner through the gaps 42. This allows the positive atomization and ejection (spraying) of the first liquid L1.

The multiple (three) points of contact 45 are spaced apart at equal angular intervals about the center 435 (about the first inner tube 44*a*). This makes it possible to establish gaps 42 that are equal in dimension. Accordingly, gas G can be ejected uniformly in the direction surrounding the first liquid L1 being ejected (circumferentially of the liquid orifice 442). This allows further positive atomization of the first liquid L1

The maximum width W of the gaps 42 is not especially limited, but is preferably 20-200 μm, more preferably 40-80 μm, where the sprayer 1 is used in laparoscopic surgery.

The radius R of the outer periphery 444 of each liquid orifice 442 is not limited to a particular dimension. Preferably, the Radius R of the outer periphery 444 of each liquid orifice 442 is 0.2-1 mm, more preferably 0.4-0.8 mm, where the sprayer 1 is used in a laparoscopic surgery.

In manufacturing the nozzle 4 so that contact is provided at three points 45 between the inner periphery 434 of the lumen 433*a* and the outer periphery 444 of the liquid orifice 442 (true for the lumen 433*b*), the outer tube 43 having the lumens 433*a*, 433*b*, the first inner tube 44*a* having the liquid orifice 442 and the second inner tube 44*b* having the liquid orifice 442 are first prepared or obtained. In this case, the distance H concerning lumen 433*a* (true for lumen 433*b*) is established nearly equal to or somewhat smaller than the radius R of liquid orifice 442.

Next, the first inner tube 44*a* is inserted in the outer tube 43 at the base thereof, to fit the lumen 433*a* with the liquid orifice 442. This places the lumen 433*a* and the liquid orifice 442 in multi-point contact (three point contact in this illustrated embodiment). Similarly, the second inner tube 44*b* is inserted in the outer tube 43 at the base thereof, to fit the lumen 433*b* with the liquid orifice 442. This places the lumen 433*b* and outer periphery 444 of liquid orifice 442 in multi-point contact (three point contact in this illustrated embodiment). It is thus possible to relatively easily manufacture the nozzle 4 so that it can eject gas relatively uniformly in a manner as mentioned before.

The structure shown in FIG. 10 provides point contacts between the inner periphery of the lumen 433*a* (as well as the lumen 433*b*) and the outer periphery 444 of the liquid orifice 442.

The embodiment shown in FIG. 10 provides the liquid orifice 442 of the first inner tube 44*a* and the liquid orifice 442 of the second inner tube 44*b* of the same size, and the lumen 433*a* and the lumen 433*b* of the same size correspondingly. Because the sprayer 1 is formed with respective lumens 433*a*, 433*b* corresponding to the liquid orifices 442, 442 of the first and second inner tubes 44*a*, 44*b*, the liquid orifices 442, 442 of the first and second inner tubes 44*a*, 44*b* can be made different in size from each other, depending upon, for example, the liquid mixture to be applied to the diseased or treatment region. That is, the liquid orifices 442, 442 of the first and second inner tubes 44*a*, 44*b* can be made different in size from each other, depending upon, for example, the nature or types of first and second liquids L1, L2 used. Correspondingly, the lumens 433a, 433b can be properly changed in size.

The nozzle 4 is preferably made in a curved (bent) shape at its tip, as required, as shown in FIG. 1. This makes it possible to relatively easily insert the tip of nozzle 4 into a lumen where the sprayer 1 is used in laparoscopic surgery.

As shown in FIG. 10 (and also in FIG. 1), a marker 437 is provided in the outer surface of the nozzle 4 (the outer tube 43) to permit visual recognition of the juxtaposing direction of the two liquid orifices 442. This makes it possible to carry out application while confirming the juxtaposing direction of two liquid orifices 442 where using the sprayer 1.

FIGS. 5-9 illustrate a volume changer 441 provided respectively at each of the first and second inner tubes 44a, 44b at positions close to the sprayer body 7 to change the interior volumes of the first and second inner tubes 44a, 44b. In the illustrated embodiment, the volume changer 441 of the first inner tube 44a is constituted by a volume changing portion of the first inner tube 44a, and the volume changer 441 of the second inner tube 44a is constituted by a volume changing portion of the second inner tube 44a. The volume changer 441 of the first inner tube 44a and the volume changer 441 of the second inner tube 44b are arranged in symmetric positions with respect to the supply tube 46.

At an intermediate point of the supply tube 46, a balloon 461 is provided to expand and contract in response to the flow rate (supply amount) of the gas G. The balloon 461 is arranged in a longitudinal position corresponding to the longitudinal position of the volume changers 441. The balloon 461 is arranged, with respect to the radial direction, between the volume changer 441 of the first inner tube 44a and the volume changer 441 of the second inner tube 44b. The balloon 461 possesses a thickness (i.e., the thickness of the tube wall of the balloon 461) smaller than the thickness of the supply tube 46 on either longitudinal end of the balloon. This helps positively assure expansion upon supplying (flowing of) gas G in the balloon 461 and contraction upon stopping the supply of the gas G. The balloon 461 serves as a means for deforming the volume changers 441 in a manner increasing and decreasing the volumes of the volume changers 441 due to the expansion and contraction.

Figure 5:
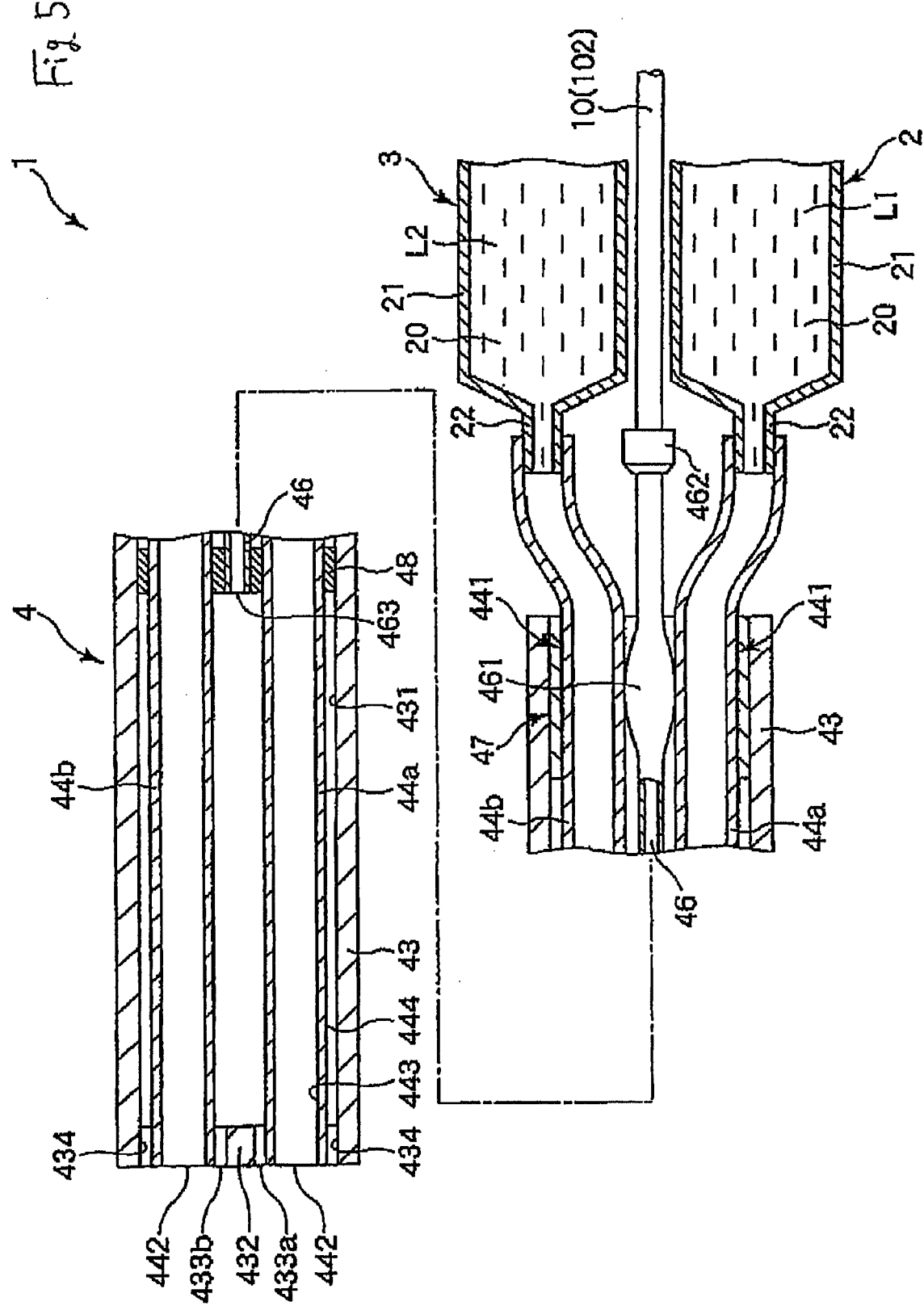
FIG. 5 is a fragmentary longitudinal cross-sectional view of the nozzle and syringe of the sprayer shown in FIG. 1, illustrating parts of the sprayer in one operational state.

As shown in FIGS. 5 and 9, the balloon 461 in its natural state (i.e., contracted to the greatest extent) has an outer diameter greater than the outer diameter of the portions of the supply tube 46 in front of and rearward of the balloon 461. In this state, the balloon 461 may contact the volume changers 441 in a manner not pressing the volume changers 441 (i.e., not reducing the volume of the volume changers 441) or may be spaced from the volume changers 441. In the arrangement shown in FIGS. 5 and 9, the balloon 461 is in contact with the volume changers 441 in a manner that does not press the volume changers to an extent causing a reduction in volume. In this case, the volume changers 441 are maximal in volume. The term "natural state" refers to the state where no external forces are applied, i.e. gas G is not supplied in the interior thereof.

Figure 6:
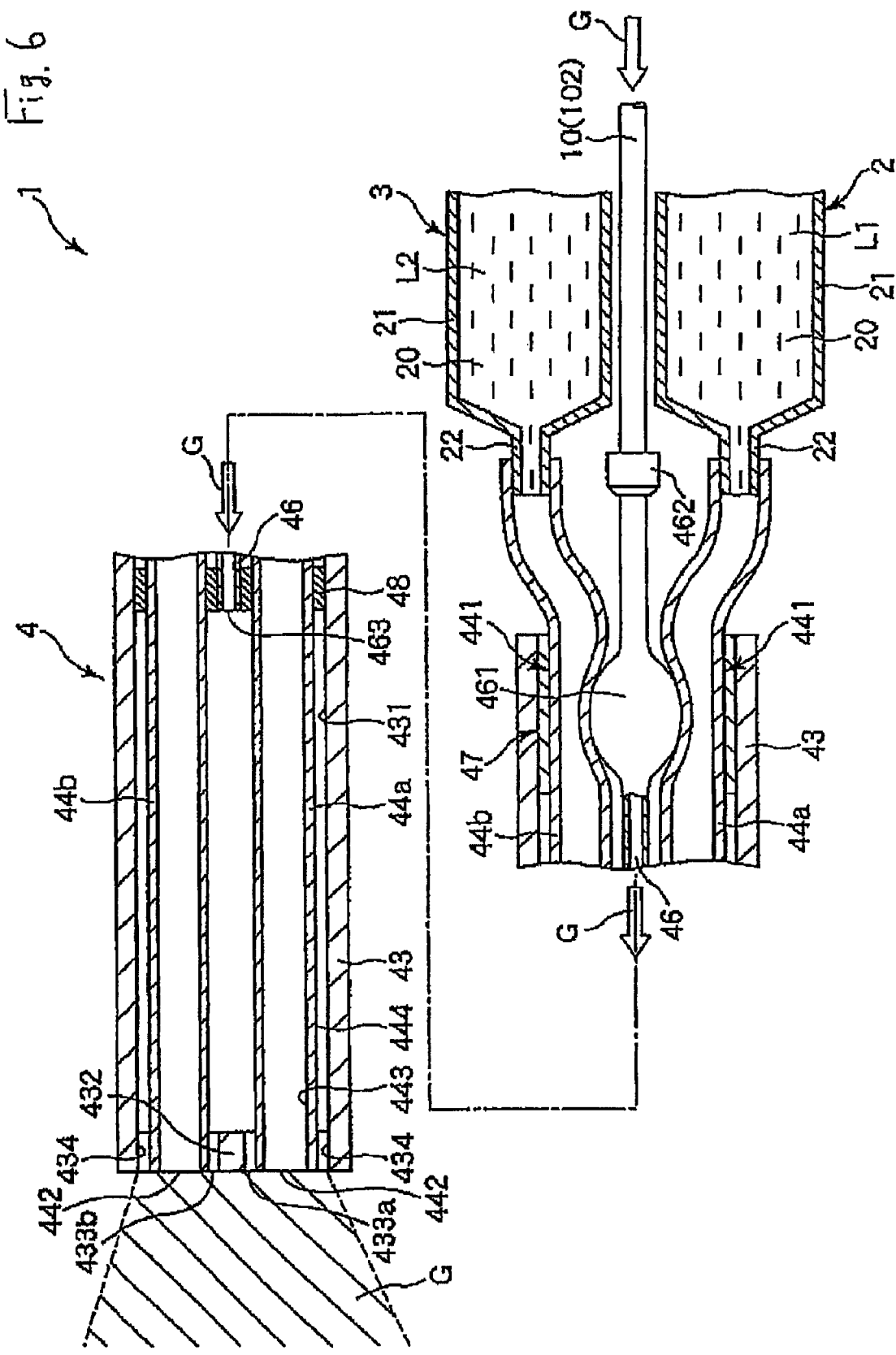
FIG. 6 is a fragmentary longitudinal cross-sectional view of the nozzle and syringe of the sprayer shown in FIG. 1, illustrating parts of the sprayer in another operational state.

As shown in FIGS. 6-8, when gas is supplied to the supply pipe 46, the balloon 461 expands by virtue of being supplied with the gas. The expanded balloon 461 presses the volume changers 441 against the elastic force of the volume changers 441. This reduces the respective volumes of the volume changers 441 (volume changing portions of the inner tubes 44a, 44b). The expanded balloon 461 presses the volume changers 441 to reduce the volume of the volume changers, but not to such a degree that the inner surfaces of the volume changers 441 are brought into close contact with each other (i.e., a state where the volume changers are completely closed off).

When the expanded balloon 461 contracts and returns toward its natural state, the volume changers 441 are released from being pressed. The volume changers 441 are thus restored in shape by their own elasticity as shown in FIG. 9.

The nozzle 4 has a ring (band) 47 holding the volume changers 441 of the respective first and second inner tubes 44a, 44b and the balloon 461 collectively from the outer tube. The ring 47 can be formed by winding a strip of plastic material, for example. The ring 47 restricts the positional relationship between the volume changers 441 and the balloon 461 irrespective of the expansion and contraction of balloon 461. Due to this, when the balloon 461 expands, the expanded balloon 461 positively presses the volume changers 441.

In this manner, in the sprayer 1, the volume changers 441 positively change in volume in response to the expansion and contraction of the balloon 461.

As shown in FIGS. 1 and 2, the fixing member 41 is arranged at the base of the nozzle 4. The fixing member 41 is a hollow member having a front opening 412 and a base opening 411. The front opening 412 is hermetically connected with the base of the outer tube 43 while the base opening 411 is secured to the front plate 72 of the sprayer body 7. Located in the interior of the fixing member 41 are a connecting portion of the first inner tube 44a with the first syringe 2, a connecting portion of the second inner tube 44b with the second syringe 3 and a connecting portion (base 462) of the supply tube 46 with tube 10. This can cover the connecting portions and hence protect those portions.

The operation of the sprayer 1 is now described, considered with reference to a usable state of the sprayer in which it is loaded with the first and second syringes 2, 3 respectively filled with the first and second liquids L1, L2 and connected to the gas-containing canister 300.

The first and second syringes 2, 3 are respectively filled with the first and second liquids L1, L2 in an amount required (sufficient) for application to a diseased or treatment region. The gas-containing canister 300 is opened at its valve 301 wherein gas G is to be supplied to sprayer 1.

In the sprayer 1, the force causing a gap 98 between the seal member 94 and the flange 95 which operates against the force of the bias member 96 urging the flange 95 on the seal member 94, i.e. the pressing force to incline the second connecting portion 92 in the direction of the arrow C from the first position into the second position, is established smaller than the force that moves the plungers 26 of the first and second syringes 2, 3 toward the front. Namely, before the movement of the plungers 26 occurs, the gap 98 arises to supply gas G. Such setting is available by properly establishing various conditions, for example, the spring constant of the bias member 96, the liquid viscosities of the liquids and the inner diameters of the outer shells 21.

In use, the user's index finger is put on the handle 751 of the sprayer body 7, the user's middle finger is put on the handle 752 and the user's thumb is placed on the presser 82 of the manipulator 8. At this time, the first liquid L1 is not supplied to the first passage 44, the second liquid L2 is not supplied to the second passage 45, and the gas G is not supplied to the third passage 46 as shown in FIG. 5. Due to this, the gas G and the first and second liquids L1, L2 are not ejected (sprayed) through the nozzle 4. In addition, because the inflatable portion 461 is not expanded, the volume changers 441, 441 are not pressed by the inflatable portion.

In this state, when the presser 82 is pushed by the thumb, the second connecting portion 92 first inclines to cause the gap 98 between the seal member 94 and the flange 95. The gas G passes through the gap 98 as generally shown in FIG. 4. This supplies gas G to the supply pipe 46 through the second tube 102, thus ejecting gas G at a high rate through the lumens 433a, 433b of the nozzle 4 as seen in FIG. 6. At this time, because the balloon 461 expands, the volume changers 441 are pressed. The expansion of the balloon 461 is maintained until terminating the supply of gas G to the balloon 461.

Meanwhile, the pushing of the presser 82 with the thumb does not yet move the manipulator 8 in its entirety, i.e. the plungers 26 are not yet moved toward front. Accordingly, first and second liquids L1, L2 are not yet supplied respectively to the first and second inner tubes 44a, 44b.

When the presser 82 is pushed further, the second connecting portion 92 inclines into a limitation so that the pressing force of the thumb is delivered to the coupler 81 through the presser 82. This causes the coupler 81 (entire manipulator 8) to begin moving, thereby pushing the first liquid L1 out of the first syringe 2 and the second liquid L2 out of the second syringe 3. The pushed out portion of the first liquid L1 passes through the volume changer 441 which remains pressed by the balloon 461 and moves toward the front, i.e. it reaches the liquid orifice 442 of the first inner tube 44a where it is ejected (sprayed) therefrom as shown in FIG. 7. Meanwhile, the second liquid L2 passes through the volume changer 441 which remains pressed by the balloon 461 in a manner similar to the first liquid L1 and reaches the liquid orifice 442 of the second inner tube 44b where it is ejected therefrom as shown in FIG. 7.

The first and second liquids L1, L2 thus ejected are entrained in the gas G ejected at a high rate. Due to this, the first and second liquids L1, L2 are atomized or turned into atomized sprays and mixed together, thus being applied to a diseased or treatment region. At this time, because the liquid orifice 442 of the first inner tube 44a is fixed relative to the lumen 433a, and the liquid orifice 442 of the second inner tube 44b is fixed relative to the lumen 433b as mentioned before, the gas G is sprayed uniformly. This makes it possible to positively atomize the first and second liquids L1, L2, thereby positively mixing the first and second liquids L1, L2 together and applying those to a diseased or treatment region.

As the pressing force of the thumb on the presser 82 (manipulator 8) is reduced after the completion of a predetermined amount of application to the diseased or treatment region, the manipulator 8 in its entirety is stopped from moving. This stops the plungers 26 from moving and hence stops the first and second liquids L1, L2 from ejecting as seen in FIG. 8. At this time, because the second connecting portion 92 is kept in a second position by the urging of the presser 82, the gas G continues to be ejected as shown in FIG. 8.

As the pressing force of the thumb on the presser 82 is reduced, the thumb urging presser 82 ultimately moves away from presser 82. Due to this, the second connecting portion 92 is canceled of the pressing force and returned to the first position. This eliminates the gap 98 from between the seal member 94 and the flange 95, and so the seal member 94 and the flange 95 at its entire outer periphery 951 are placed in close contact in the manner seen in FIG. 3. At this time, the gas G is stopped from being supplied to the supply pipe 46. Hence, gas G is no longer ejected at the lumens 433a, 433b as illustrated in FIG. 9.

When the gas G is stopped from being supplied to the supply pipe 46, the balloon 461 contracts in the manner depicted in FIG. 9. This cancels the pressing of the balloon 461 on the volume changers 441, thus increasing the volumes of the volume changers 441 greater than the volumes in the state where the liquid (first and second liquids L1, L2) is being ejected. By thus increasing the volumes, the first liquid L1 at the tip P1 of the liquid orifice 442 of the first inner tube 44a is retracted rearwardly, while the second liquid L2 at the tip P2 of the liquid orifice 442 of the second inner tube 44b is retracted rearwardly as seen in FIG. 9.

By retracting the first and second liquids L1, L2 at the respective front ends P1, P2 in this manner, the first and second liquids L1, L2 can be prevented from being mixed together in the vicinity of the liquid orifices 442 of the first and second inner tubes 44a, 44b and can thus be prevented from forming a gelatinous form or mass in the vicinity of the liquid orifices 442 of the first and second inner tubes 44a, 44b. This helps positively prevent the clogging (adhesion of a solidified substance due to the mixing of the first and second liquids L1, L2 together) in the liquid orifices 442 of the first and second inner tubes 44a, 44b and the peripheral lumens 433a, 433b after the use of sprayer 1 (after the completion of application). The sprayer 1 in a state free from clogging can then be again used for the application to a diseased region. On this occasion, uniform ejection of the gas G is done, hence enabling the application of a liquid mixture in which the first and second liquids L1, L2 are uniformly mixed together.

Meanwhile, the sprayer 1 is constructed to eject (spray) gas G in advance of the first and second liquids L1, L2 through the nozzle 4. This can help prevent the first and second liquids L1, L2 solely from being ejected and applied to a diseased or treatment region. In addition, owing to the gas G ejected (sprayed) in advance, the first and second liquids L1, L2 are both positively sprayed in atomized forms. Hence, those liquids are positively mixed together.

The sprayer 1 is also constructed to stop the gas G from ejecting later in timing than the first and second liquids L1, L2 (i.e., the gas ejection stops after the ejection of the liquids L1, L2 ends). Due to this, where liquids remains at the orifices because of stopping the liquids from ejecting, the remaining liquid can be blown away by the gas G. Therefore, it is possible to more positively prevent the trouble (e.g., clogging resulting from solidification) caused by the reaction of the first and second liquids L1, L2 at the liquid orifices 442 of the first and second inner tubes 44a, 44b and the peripheral lumens 433a, 433b. Sprayer 1 in a state free from clogging can be again used for the application to a diseased region. In the case that the sprayer 1 is again used, the gas G is ejected uniformly, hence applying a liquid mixture in which the first liquid L1 and the second liquid L2 are uniformly mixed together.

Figure 11:
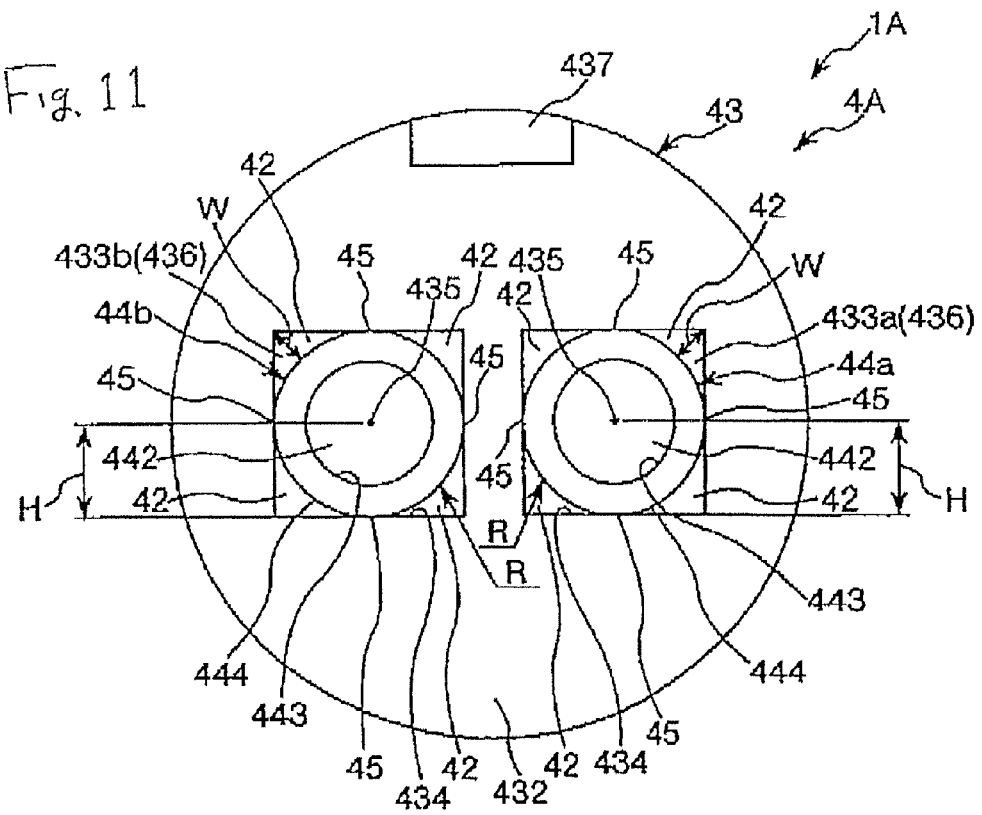
FIG. 11 is a front view of a nozzle of a sprayer according to a second embodiment.

FIG. 11 illustrates a second embodiment of a nozzle of a sprayer disclosed here. The following description primarily describes aspects of the sprayer that differ from the foregoing embodiment. Features of this embodiment that are the same as those described above are identified by the same reference numeral and a detailed description of such features is not repeated.

The present embodiment is similar to the first embodiment, except that the gas orifice has a different form. In the sprayer 1A shown in FIG. 11, the nozzle 4A has two lumens 433a, 433b whose inner peripheries 434 each possess a square shape or form. Because the inner peripheries 434 of the two lumens 433a, 433b are the same, the following explanation describes one of the lumens 433a and the associated liquid orifice 442 of the first inner tube 44a arranged inside the lumen 433a.

Contact between the inner periphery 434 of the lumen 433a and the outer periphery 444 of the liquid orifice 442 of the first inner tube 44a is provided at four points 45. Those contact points 45 are circumferentially spaced apart at equal angular intervals about the center 435. A space exists between the outer periphery of the liquid orifice 442 and the inner periphery of the lumen 433*a* (gas orifice) at regions between circumferentially adjacent contact points 45.

The number of contact points in this embodiment is greater than that of the arrangement of the lumen 433*a* and the liquid orifice 442 of the first embodiment. By virtue of the arrangement or configuration of the lumen 433*a* and the liquid orifice 442, the liquid orifice 442 is fixed more positively to the lumen 433*a*. In addition, because of the distributed arrangement of the gas orifice 436 (distributed arrangement of the portions of the gas orifice 436), gas G can be ejected (sprayed) further uniformly.

Due to this, the gas G is can be ejected positively and uniformly through four gaps 42, thereby ejecting the first liquid L1 with positive atomization. Similarly, the gas G can be ejected positively and uniformly also at the lumen 433*b* through the four gaps 42, thereby ejecting the second liquid L2 with positive atomization. In addition, the atomized first liquid L1 and the atomized second liquid L2 are positively mixed together.

Figure 12:
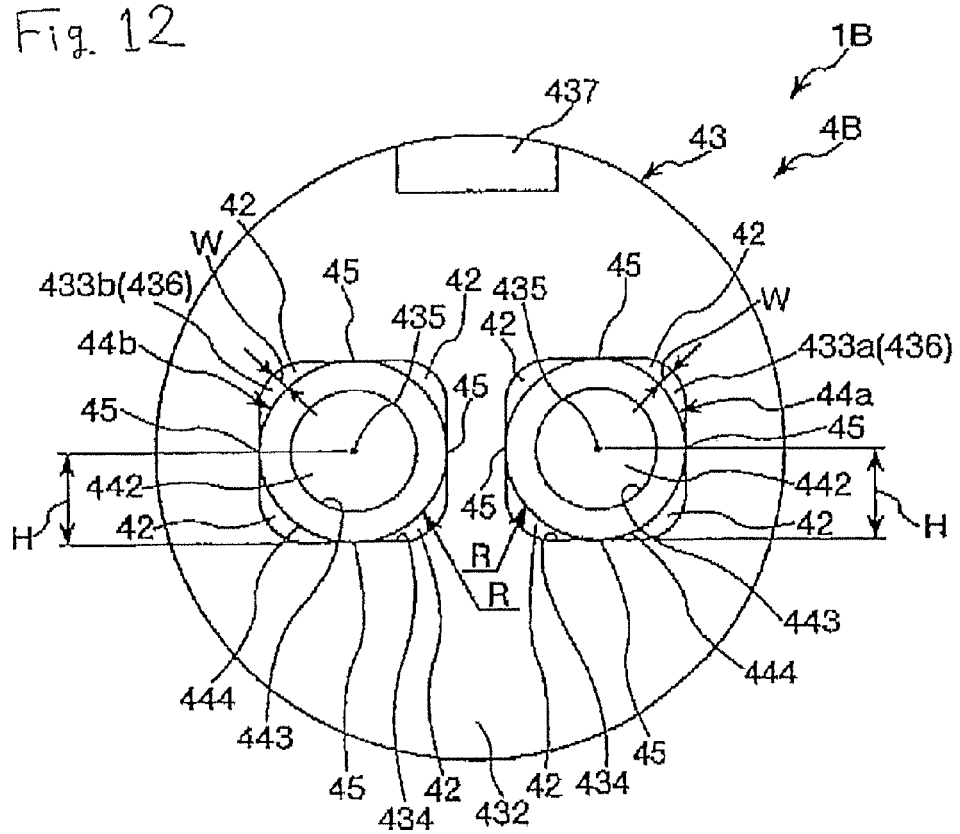
FIG. 12 is a front view of a nozzle of a sprayer according to a third embodiment.

FIG. 12 illustrates a third embodiment of a nozzle of a sprayer disclosed here. The following description primarily describes aspects of the sprayer that differ from the foregoing embodiments. Features of this embodiment that are the same as those described above are identified by the same reference numeral and a detailed description of such features is not repeated.

The present embodiment is similar to the second embodiment, except that the gas orifice has a different form. The nozzle 4B of the sprayer 1B shown in FIG. 12 has lumens 433*a*, 433*b* whose inner peripheries 434 each possess a square shape or form, with rounded corners. With this arrangement, the maximum width W of the gaps 42 is smaller than the maximum width W of the gaps 42 of the second embodiment, thus increasing the flow speed of the gas G ejected (sprayed) through the gaps 42. This helps contribute to a positive atomization of the liquid mixture (liquid) with a smaller amount of gas.

Figure 13:
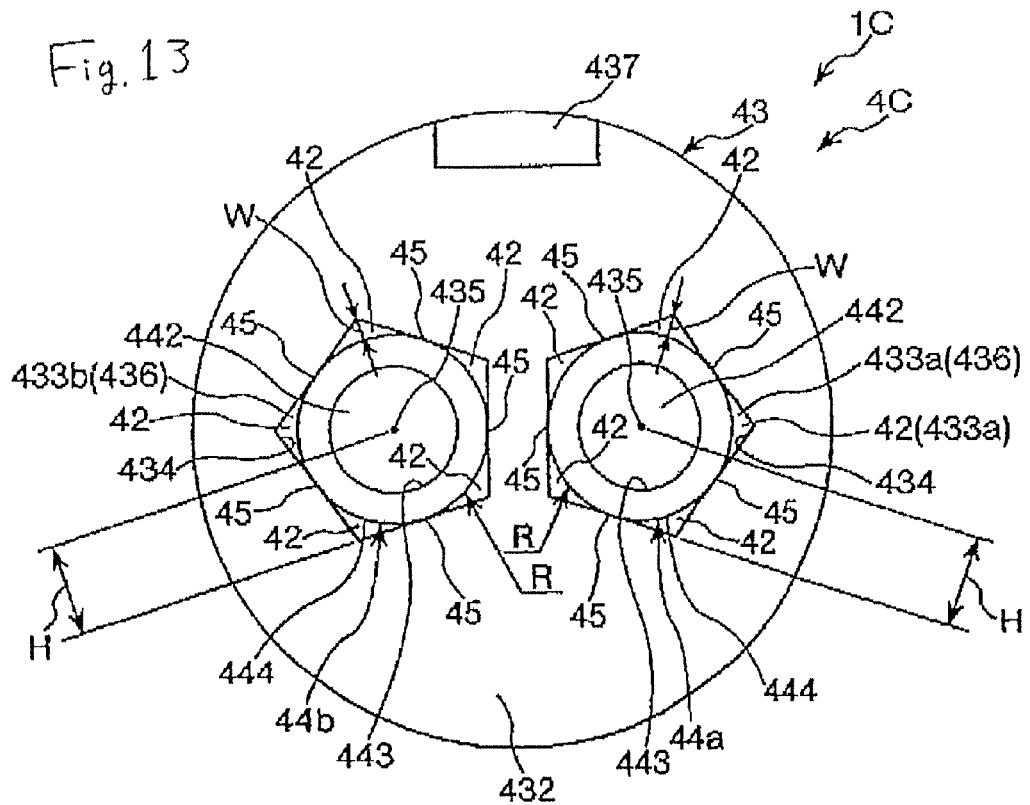
FIG. 13 is a front view of a nozzle of a sprayer according to a fourth embodiment.

FIG. 13 illustrates a fourth embodiment of a nozzle of a sprayer disclosed here. The following description primarily describes aspects of the fourth embodiment that differ from the foregoing embodiments. Features of this embodiment that are the same as those described above are identified by the same reference numeral and a detailed description of such features is not repeated.

The present embodiment is similar to the first embodiment, except that the gas orifice has a different form. The sprayer 1C shown in FIG. 13 includes the nozzle 4C having lumens 433*a*, 433*b* whose inner peripheries 434 each possess a regular pentagonal shape or form. Because the inner peripheries 434 of both lumens 433*a*, 433*b* are of the same form, the following explanation will describe the lumen 433*a* and the liquid orifice 442 of the first inner tube 44*a* arranged inside the inner lumen 433*a*, and such description applies to the lumen 433*b* and the liquid orifice 442 of the second inner tube 44*b*.

In this embodiment, contact 45 between the inner periphery 434 of the lumen 433*a* and the outer periphery 444 of the liquid orifice 442 of the first inner tube 44*a* is provided at five contact points. Those five contact points 45 are circumferentially spaced apart at equal angular intervals about the center 435. Also, a space or gap exists between the outer periphery of the liquid orifice 442 and the inner periphery of the lumen 433*a* (gas orifice) at regions between the circumferentially adjacent contact points 45.

Because the number of contact points is greater than that of the arrangement of the lumen 433*a* and the liquid orifice 442 of the first embodiment by virtue of the arrangement of lumen 433*a* and liquid orifice 442, the liquid orifice 442 is fixed more positively to the lumen 433*a*. This helps ensure a positive and uniform ejection (spraying) of the gas G through five gaps 42, thereby ejecting the first liquid L1 with a positive atomization. Similarly, the lumen 433*b* is also allowed to positively and uniformly eject the gas G through five gaps 42, thereby positively ejecting the second liquid L2 with a positive atomization. In addition, the atomized first liquid L1 and the atomized second liquid L2 are mixed positively.

With the greater degree of polygon (i.e., the more corners/sides), the ejection of gas G becomes more uniform to enable spraying at a smaller amount of gas. However, if the number of corners increases excessively, it is difficult to obtain a gas passage.

Figure 14:
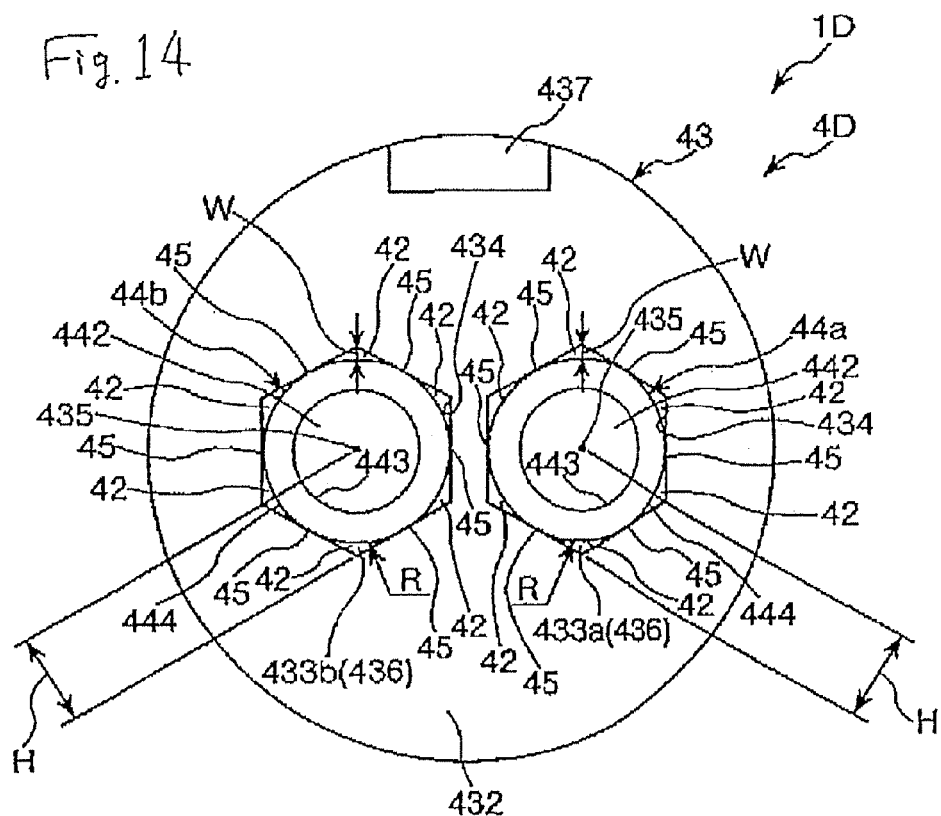
FIG. 14 is a front view of a nozzle of a sprayer according to a fifth embodiment.

FIG. 14 illustrates a fifth embodiment of a nozzle of a sprayer disclosed here. The following description primarily describes aspects of the fifth embodiment that differ from the foregoing embodiments. Features of this embodiment that are the same as those described above are identified by the same reference numeral and a detailed description of such features is not repeated.

This fifth embodiment is similar to the first embodiment, except that the gas orifice has a different form. In the sprayer 1D shown in FIG. 14, the nozzle 4D has two lumens 433*a*, 433*b* whose inner peripheries 434 each possess a regular hexagonal form or shape. Because the inner peripheries 434 of both the lumens 433*a*, 433*b* possess the same shape or form, the following explanation about the lumen 433*a* and the liquid orifice 442 of the first inner tube 44*a* arranged inside the lumen 433*a* applies equally to the other lumen 433*b* and the liquid orifice 442 of the second inner tube 44*b* arranged inside the lumen 433*b*.

In this embodiment, contact is provided at six contact points 45 between the inner periphery 434 of the lumen 433*a* and the outer periphery 444 of the liquid orifice 442 of the first inner tube 44*a*. Those contact points 45 are spaced apart at equal angular intervals about the center 435. A space or gap exists between the outer periphery of the liquid orifice 442 and the inner periphery of the lumen 433*a* (gas orifice) at regions between the circumferentially adjacent contact points 45.

Because the number of contact points in this embodiment is greater than that of the arrangement of the lumen 433*a* and the liquid orifice 442 of the first embodiment by virtue of the arrangement or configuration of the lumen 433*a* and the liquid orifice 442, the liquid orifice 442 is fixed more positively to the lumen 433*a*. This helps ensure that the gas G is positively and uniformly ejected (sprayed) through the six gaps 42, thereby ejecting the first liquid L1 with a positive atomization. Similarly, the lumen 433*b* also ejects gas G positively and uniformly through the six gaps 42, thereby ejecting the second liquid L2 with a positive atomization. In addition, the atomized first liquid L1 and the atomized second liquid L2 are positively mixed together.

Figure 15:
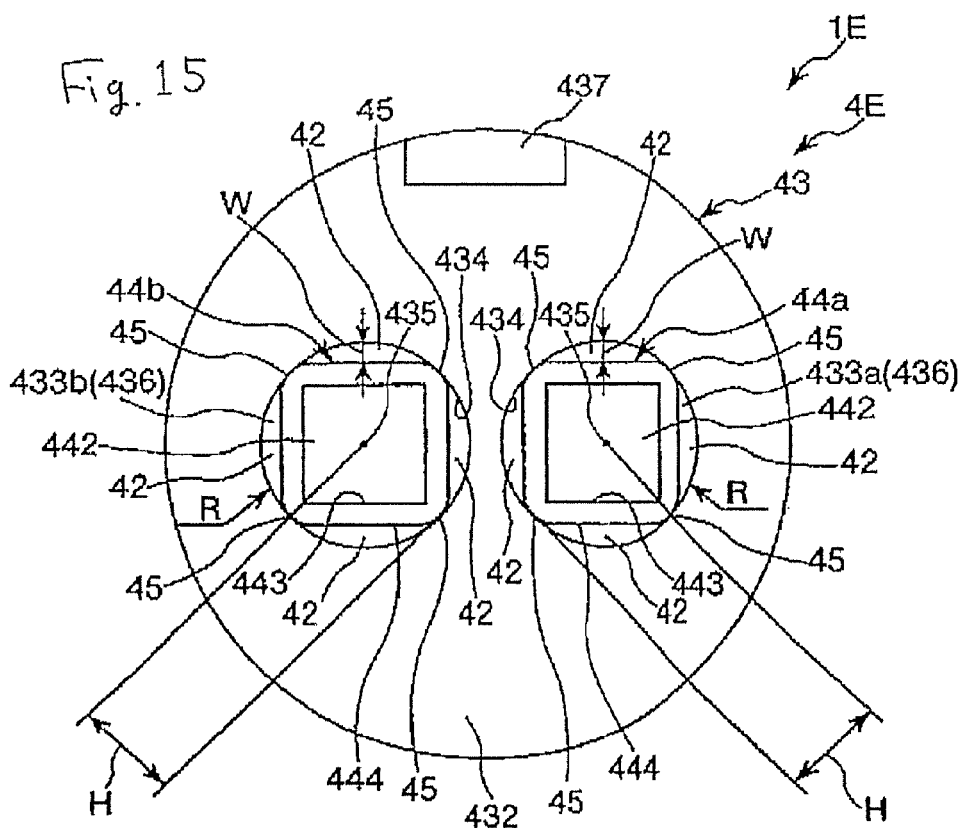
FIG. 15 is a front view of a nozzle of a sprayer according to a sixth embodiment.

FIG. 15 illustrates a sixth embodiment of a nozzle of a sprayer disclosed here. The following description primarily describes aspects of the sixth embodiment that differ from the foregoing embodiments. Features of this embodiment that are the same as those described above are identified by the same reference numeral and a detailed description of such features is not repeated.

The sixth embodiment is similar to the first embodiment, except that the gas orifice and the liquid orifice respectively have different forms. In the sprayer 1E shown in FIG. 15, the nozzle 4E has the first inner tube 44a and the second inner tube 44b in which the outer peripheries 444 of the liquid orifice 442 each possess a square shape or form, rounded at the corners as illustrated. The lumens 433a, 433b have respective inner peripheries 434 that are each circular in shape or form. The lumen 433a (the same as the lumen 433b) possessing such a form has an inner periphery 434 whose radius R is established nearly equal to or somewhat smaller than the distance (length) H between the center 435 of the liquid orifice 442 and each side.

Because the positional relationship between the lumen 433a and the liquid orifice 442 of the first inner tube 44a is the same as the positional relationship between the lumen 433b and the liquid orifice 442 of the second inner tube 44b, the following explanation about the positional relationship between the lumen 433a and the liquid orifice 442 of the first inner tube 44a also applies to the positional relationship between the lumen 433b and the liquid orifice 442 of the second inner tube 44b.

By virtue of the form or shape of the inner periphery 434 of the lumen 433a and the outer periphery 444 of the liquid orifice 442 of the first inner tube 44a, contact between the inner periphery 434 of the lumen 433a and the outer periphery 444 of the liquid orifice 442 exists at four points 45. With this construction, when the first liquid L1 is ejected (sprayed) together with the gas G through the lumen 433a (nozzle 4), the liquid orifice 442 is positively restricted from deviating in the radial direction under the pressure, for example, of gas G, i.e., the liquid orifice 442 is positively fixed relative to the lumen 433a. This helps maintain constant gaps (clearances) 42 between inner periphery 434 of lumen 433a and outer periphery 444 of liquid orifice 442 so that the gaps or clearances are not closed or obstructed, thereby allowing the gas G to be ejected positively and uniformly through the gaps 42. Consequently, the first liquid L1 is ejected (sprayed) with a positive atomization.

The four contacts 45 are spaced apart at equal angular intervals about center 435. This makes it possible to establish gaps 42 equal in size to one another between circumferentially adjacent contact points, thereby uniformly ejecting gas G in the direction surrounding the first liquid L1 being ejected. Consequently, the first liquid L1 is positively atomized.

Although the outer periphery 444 of each liquid orifice 442 is in a square form (shape) with rounded corners, it is not limitative but may be in a square form.

FIG. 16 illustrates a seventh embodiment of a nozzle of a sprayer disclosed here. The following description primarily describes aspects of the seventh embodiment that differ from the foregoing embodiments. Features of this embodiment that are the same as those described above are identified by the same reference numeral and a detailed description of such features is not repeated.

This seventh embodiment is similar to the sixth embodiment, except that the liquid orifice has a different form or shape.

In the sprayer 1F shown in FIG. 16, the nozzle 4F has the liquid orifices 442 whose outer peripheries 444 (also true for the inner peripheries 443) each possess a regular pentagonal form or shape. Because the outer periphery 444 of the liquid orifice 442 of the first inner tube 44a and the outer periphery 444 of the liquid orifice 442 of the second inner tube 44b are the same in shape or form, the following description of the liquid orifice 442 of the first inner tube 44a and the lumen 433a applies equally to the liquid orifice 442 of the second inner tube 44b and the lumen 433b.

In this embodiment, contact between the outer periphery 444 of the liquid orifice 442 of the first inner tube 44a and the inner periphery 434 of the lumen 433a exists at five points 45. Those contact points 45 are spaced apart at equal angular intervals about the center 435. A space or gap exists between the outer periphery of the liquid orifice 442 and the inner periphery of the lumen 433a (gas orifice) at regions between the circumferentially adjacent contact points 45.

The number of contact points in this embodiment is greater than the number of contact points of the liquid orifice 442 and lumen 433a in the sixth embodiment by virtue of the configuration of the liquid orifice 442 and the lumen 433a. With this arrangement according to the seventh embodiment, the liquid orifice 442 is fixed more positively relative to the lumen 433a.

FIG. 17 depicts an eighth embodiment of a nozzle of a sprayer disclosed here. The following description primarily describes aspects of the eighth embodiment that differ from the foregoing embodiments. Features of this embodiment that are the same as those described above are identified by the same reference numeral and a detailed description of such features is not repeated.

The present embodiment is similar to the first embodiment, except that the form (shape) and number of gas orifices is different. Referring to FIG. 17, the sprayer 1G includes a nozzle 4G having a gas orifice 436 possessing a single (one) lumen 433c. The liquid orifice 442 of the first inner tube 44a and the liquid orifice 442 of the second inner tube 44b are arranged collectively inside the lumen 433c.

As shown in FIG. 17, the lumen 433c has an inner periphery 434 possessing a rectangular form or shape, with a longer side of length M1 established equal to or somewhat smaller than two times the radius R of the outer periphery of one orifice 442 plus two times the radius R of the outer periphery of the other orifice 442. Thus, with both orifices 442, 442 having the same outer diameter R, the length of the longer side M1 is equal to or somewhat smaller than R×4.

The liquid orifices 442, arranged inside the lumen 433c, have outer peripheries 444 contacting the inner periphery 434 of the lumen 433c at three points 45. Meanwhile, the outer peripheries 444 of the liquid orifices 442 are in point-contact with each other at one point. A space or gap exists between the outer periphery of the liquid orifice 442 and the inner periphery of the lumen 433a (gas orifice) at regions between the circumferentially adjacent contact points 45.

By virtue of this arrangement, the liquid orifices 442 are positively fixed relative to the lumen 433c (gas orifice 436). The spacing (pitch) between the liquid orifices 442 is smaller than that of the first embodiment. Due to this, when the first and second liquids L1, L2 are ejected, the liquids are mixed together further positively.

In the sprayer 1G, the structure of the nozzle 4G is simplified because the two inner tubes (the first inner tube 44a and the second inner tube 44b) are arranged in a single (only one) lumen 433c. This relatively simple structure allows the first and second inner tubes 44a, 44b to be comparatively accurate in position relative to the lumen 433c.

The inner periphery 434 of the lumen 433c is not limited to being rectangular in shape, but may be octagonal in shape in which two regular pentagons share their one sides, for example.

Figure 18:
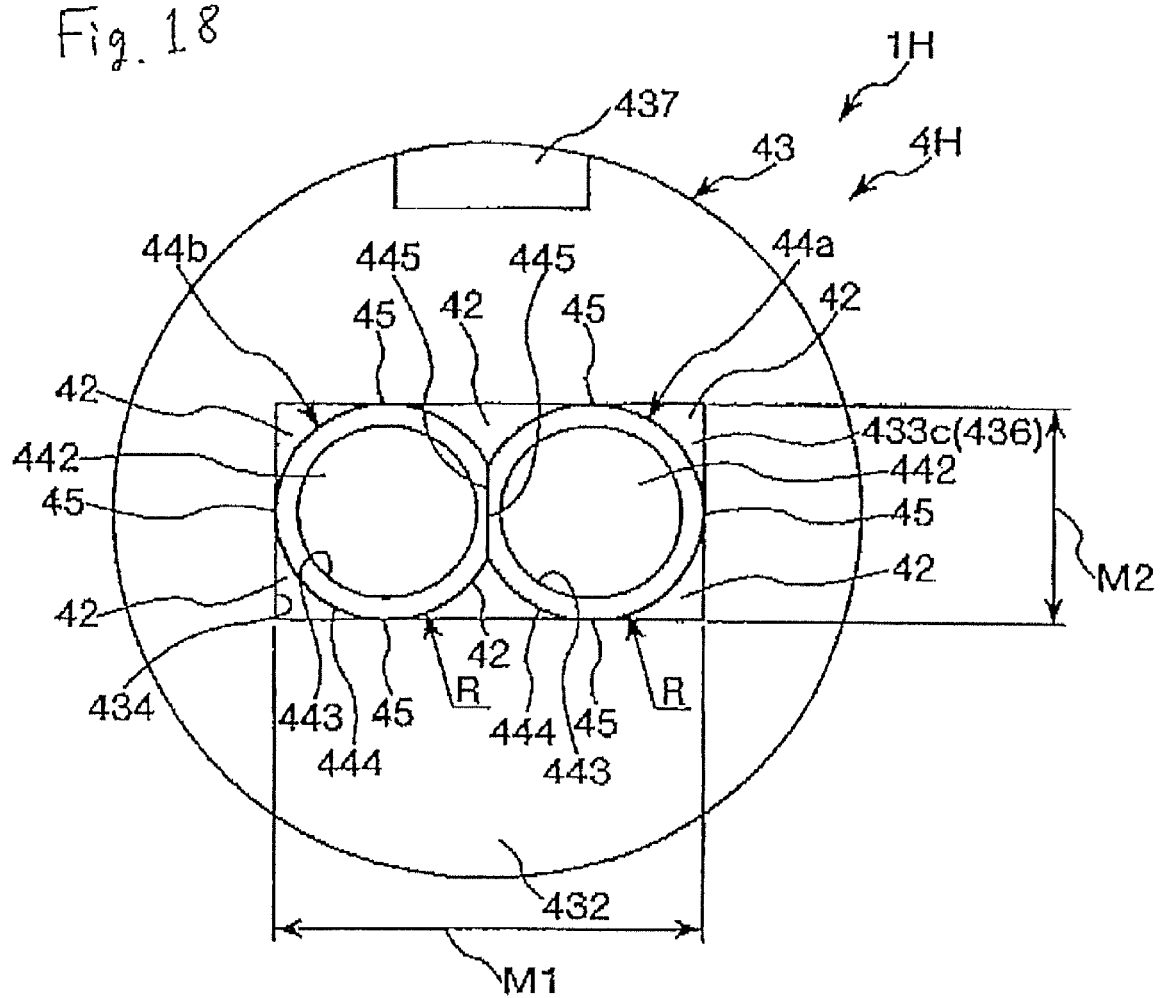
FIG. 18 is a front view of a nozzle of a sprayer according to a ninth embodiment.

FIG. 18 depicts a ninth embodiment of a nozzle of a sprayer disclosed here. The following description primarily describes aspects of the ninth embodiment that differ from the foregoing embodiments. Features of this embodiment that are the same as those described above are identified by the same reference numeral and a detailed description of such features is not repeated.

This ninth embodiment is similar to the eighth embodiment, except that the liquid orifice has a different form. As illustrated in FIG. 18, the nozzle 4H of the sprayer 1H includes chords 445 (longitudinally extending flat surface portions) that are respectively formed in the outer peripheries 444 of the liquid orifices 442, wherein the chords 445 are in abutment against each other. Due to this, two liquid orifices 442 are in line-contact with each other at the outer peripheries 444 thereof, rather than point-contact.

By virtue of this arrangement, the spacing (pitch) of both liquid orifices 442 can be reduced compared to the spacing in the eighth embodiment. Due to this, when the first and second liquids L1, L2 are ejected, the liquids can be mixed together further positively.

In the sprayer 1H shown in FIG. 18, the structure of nozzle 4H can be simplified because two inner tubes (first inner tube 44a and second inner tube 44b) are arranged in a single (only one) lumen 433c in a manner similar to the eighth embodiment. With this relatively simple structure, the first and second inner tubes 44a, 44b are comparatively accurately positioned relative to lumen 433c.

The chords (flat surface portions) 445 of the respective liquid orifices 442 are not limited to being in abutment, but may be bonded together (e.g., by way of an adhesive or solvent) for example.

The sprayer disclosed here has been described based on the illustrated embodiments, but the invention is not limited to such embodiments. Various parts constituting the sprayer can be replaced with alternatives that exhibit the same or similar/equivalent functions. Additional features can also be added. Also, the sprayer may be a combination of two or more structures (features) of the foregoing embodiments.

The sprayer is assembled by loading the two syringes thereon so that two types of liquids different in liquid composition can be ejected with mixing from the syringes. However, this is not limitative as one syringe may be structurally loaded so that one type of liquid can be ejected from the syringe.

The principles, embodiments and modes of operation of the sprayer have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sprayer used in a medical procedure and having a front end, the sprayer comprising:
   a sprayer body on which are mounted a first liquid-containing tube containing a first liquid and a second liquid-containing tube containing a second liquid whose composition differs from a composition of the first liquid;
   a nozzle extending forwardly from the sprayer body, the nozzle comprising:
   a first inner tube connected to the liquid-containing first tube and through which is to flow the first liquid;
   a second inner tube connected to the liquid-containing second tube and through which is to flow the second liquid;
   an outer tube having an interior in which are positioned the first and second tubes, the outer tube being adapted to be connected to a gas source to supply gas to the interior of the outer tube;
   the outer tube comprising a front wall positioned at a front tip of the outer tube, the front wall being provided with a through opening forming a gas orifice through which the gas supplied to the interior of the outer tube is to be ejected, the gas orifice possessing an inner periphery possessing a shape;
   the first inner tube having a first tip end positioned in the gas orifice and possessing an outer periphery;
   the inner periphery of the gas orifice and the outer periphery of the first tip end being differently configured relative to one another such that the outer periphery of the first tip end and the inner periphery of the gas orifice contact one another at a plurality of circumferentially spaced apart contact points separated from one another by spaces between the outer periphery of the first tip end and the inner periphery of the gas orifice,
   wherein the gas orifice includes a first lumen in which the first tip end is disposed, an inner periphery of the first lumen having a polygonal cross-section, the outer periphery of the first tip end being of circular cross-section, wherein said contact points lie at equal angular intervals about a center of the first lumen, and said spaces have equal respective dimensions.

2. The sprayer according to claim 1, wherein the second inner tube has a second tip end positioned in the gas orifice, the inner periphery of the gas orifice and the outer periphery of the second tip end being differently configured relative to one another such that the outer periphery of the second tip end and the inner periphery of the gas orifice contact one another at a plurality of circumferentially spaced apart contact points separated from one another by spaces between the outer periphery of the second tip end and the inner periphery of the gas orifice, wherein the gas orifice includes a second lumen in which the second tip end is disposed, an inner periphery of the second lumen having a polygonal cross-section, the outer periphery of the second tip end being of circular cross-section, wherein said contact points lie at equal angular intervals about a center of the second lumen, and said spaces have equal respective dimensions.

3. The sprayer according to claim 1, wherein the inner periphery of the first lumen is of triangular cross-section to form three said contact points.

4. The sprayer according to claim 1, wherein the inner periphery of the first lumen is of square cross-section, to form four said contact points.

5. The sprayer according to claim 1, wherein the inner periphery of the first lumen is of pentagonal cross-section, to form five said contact points.

6. A sprayer having a front end from which a composition is sprayed, the sprayer comprising:
   first and second inner tubes through which is adapted to pass liquid to form the composition;
   an outer tube having an interior in which is positioned at least a first of the inner tubes and through which gas is adapted to flow;
   the first inner tube possessing a liquid orifice opening at a first tip end of the first inner tube from which the liquid is adapted to be ejected;
   the outer tube possessing a gas orifice opening at a tip end of the outer tube from which the gas is adapted to be ejected;
   the first tip end, viewed from the front end of the sprayer, possessing an outer periphery that is circular in shape;

the gas orifice, viewed from the front end of the sprayer, including a first lumen possessing an inner periphery that is polygonal in shape with rounded corners;

the outer periphery of the first tip end and the inner periphery of the first lumen being in point contact with each other at a plurality of spaced apart contact points so that the first tip end is fixed in position relative to the first lumen, with a space formed between the outer periphery of the first tip end and the inner periphery of the first lumen at regions between circumferentially adjacent contact points, wherein the contact points lie at equal angular intervals about a center of the first lumen, and said spaces have equal respective dimensions.

7. The sprayer according to claim 6, wherein the second inner tube is disposed in the interior of the outer tube, the second inner tube possessing a liquid orifice opening at a second tip end of the second inner tube from which a liquid is adapted to be ejected; the second tip end, viewed from the front end of the sprayer, possessing an outer periphery that is circular in shape; the gas orifice, viewed from the front end of the sprayer, including a second lumen possessing an inner periphery that is polygonal in shape with rounded corners; the outer periphery of the first tip end and the inner periphery of the second lumen being in point contact with each other at a plurality of spaced apart contact points so that the second tip end is fixed in position relative to the second lumen, with a space formed between the outer periphery of the second tip end and the inner periphery of the second lumen at regions between circumferentially adjacent contact points; wherein the contact points lie at equal angular intervals about a center of the second lumen, and said spaces have equal respective dimensions.

8. The sprayer according to claim 7, further comprising a tube containing the liquid and connected to at least one of the first and second inner tubes, and a container containing the gas and connected to the interior of the outer tube.

9. The sprayer according to claim 7, further comprising a volume changer member provided at an intermediate point of each inner tube, and an expandable and contractable balloon positioned adjacent the volume changer member of each inner tube and connected to a fluid source which is adapted to supply fluid to the balloon to expand the balloon to cause the balloon to press against the volume changer member to reduce a volume of the volume changing member.

10. The sprayer according to claim 6, wherein the inner periphery of the first lumen is of square cross-section, so there are four said contact points.

11. A sprayer having a front end, the sprayer comprising:
a sprayer body on which is mounted a first liquid-containing tube containing a first liquid;
a nozzle extending forwardly from the sprayer body, the nozzle comprising:
a first inner tube connected to the liquid-containing first tube and through which is to flow the first liquid;
an outer tube having an interior in which is positioned the first tube, the outer tube being adapted to be connected to a gas source to supply gas to the interior of the outer tube;
the outer tube provided with a through opening forming a first lumen through which the gas supplied to the interior of the outer tube is to be ejected, the first lumen possessing an inner periphery having a square cross-section;
the first inner tube having a first tip end positioned in the first lumen and possessing a circular outer periphery,
such that the outer periphery of the first tip end and the inner periphery of the first lumen contact one another at a plurality of circumferentially spaced apart contact points separated from one another by spaces format between the outer periphery of the first inner tube and the inner periphery of the first lumen, wherein the contact points lie at equal angular intervals about a center of the first lumen, and said spaces have equal respective dimensions.

12. The sprayer according to claim 11, further including a second liquid-containing tube containing a second liquid whose composition differs from a composition of the first liquid, the second liquid-containing tube mounted on the sprayer body; a second inner tube connected to the liquid-containing second tube and through which is to flow the second liquid; wherein the through opening of the front wall forms a second lumen through which the gas supplied to the interior of the outer tube is to be ejected; the first lumen possessing an inner periphery having a square cross-section; the second inner tube having a second tip end positioned in the gas orifice and having a circular cross-section, such that the outer periphery of the second tip end and the inner periphery of the second lumen contact one another at a plurality of circumferentially spaced apart contact points separated from one another by spaces formed between the outer periphery of the second inner tube and the inner periphery of the second lumen, wherein such contact points lie at equal angular intervals about a center of the second lumen, and said spaces have equal respective dimensions.

\* \* \* \* \*